US008571640B2

(12) United States Patent
Holman

(10) Patent No.: US 8,571,640 B2
(45) Date of Patent: Oct. 29, 2013

(54) CATHETER BASED MID-INFRARED REFLECTANCE AND REFLECTANCE GENERATED ABSORPTION SPECTROSCOPY

(75) Inventor: Hoi-Ying N Holman, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 339 days.

(21) Appl. No.: 10/582,422

(22) PCT Filed: Dec. 10, 2004

(86) PCT No.: PCT/US2004/041428
§ 371 (c)(1),
(2), (4) Date: Jun. 9, 2006

(87) PCT Pub. No.: WO2005/059510
PCT Pub. Date: Jun. 30, 2005

(65) Prior Publication Data
US 2007/0078348 A1   Apr. 5, 2007

Related U.S. Application Data

(60) Provisional application No. 60/529,073, filed on Dec. 11, 2003.

(51) Int. Cl.
*A61B 6/00*   (2006.01)
(52) U.S. Cl.
USPC .............................. 600/476; 600/473; 600/478
(58) Field of Classification Search
USPC .......... 600/476, 433, 473, 434, 462, 466, 467
See application file for complete search history.

(56) References Cited

U.S. PATENT DOCUMENTS

| | | | | |
|---|---|---|---|---|
| 4,817,013 A | * | 3/1989 | Corenman et al. | 702/30 |
| 4,913,142 A | * | 4/1990 | Kittrell et al. | 606/7 |
| 5,197,470 A | * | 3/1993 | Helfer et al. | 600/342 |
| 5,293,872 A | * | 3/1994 | Alfano et al. | 600/475 |
| 6,129,667 A | * | 10/2000 | Dumoulin et al. | 600/424 |
| 6,697,665 B1 | * | 2/2004 | Rava et al. | 600/475 |
| 2001/0047137 A1 | * | 11/2001 | Moreno et al. | 600/475 |
| 2001/0048077 A1 | * | 12/2001 | Afanassieva | 250/339.08 |
| 2002/0151774 A1 | * | 10/2002 | Soller et al. | 600/318 |
| 2002/0164810 A1 | * | 11/2002 | Dukor et al. | 436/64 |

OTHER PUBLICATIONS

Holman, et al, Mid-infrared reflectivity of experimental atheromas, JBO Letters, Journal of Biomedical Optics, vol. 13(3), May/Jun. 2008.

* cited by examiner

*Primary Examiner* — Tse Chen
*Assistant Examiner* — Joel F Brutus
(74) *Attorney, Agent, or Firm* — Michelle Chew Wong; Lawrence Berkeley National Laboratory

(57) ABSTRACT

A method of characterizing conditions in a tissue, by (a) providing a catheter that has a light source that emits light in selected wavenumbers within the range of mid-IR spectrum; (b) directing the light from the catheter to an area of tissue at a location inside a blood vessel of a subject; (c) collecting light reflected from the location and generating a reflectance spectra; and (d) comparing the reflectance spectra to a reference spectra of normal tissue, whereby a location having an increased number of absorbance peaks at said selected wavenumbers indicates a tissue inside the blood vessel containing a physiological marker for atherosclerosis.

21 Claims, 10 Drawing Sheets

CATHETER BASED MID-INFRARED REFLECTANCE AND REFLECTANCE GENERATED ABSORPTION SPECTROSCOPY

CROSS-REFERENCE TO RELATED APPLICATIONS

This application relates to and claims priority to Provisional Patent Application Ser. No. 60/529,073, filed on Dec. 11, 2003, which is hereby incorporated by reference in its entirety.

STATEMENT OF GOVERNMENTAL SUPPORT

This invention was made during work supported by U.S. Department of Energy under Contract No. DE-AC03-76SF00098. The government has certain rights in this invention.

BACKGROUND OF THE INVENTION

1. Field of the Invention

The present invention relates a reflectance-absorption spectroscopy method for the in vivo characterization and imaging of chemical composition and molecular features in abnormal tissues that are present in but are not limited to vascular diseases such as atherosclerosis. Through the use of a broad-band photon source that emits light in the mid-infrared (MIR) region, reflectance spectrographs and reflectance generated absorption spectrographs of segments of normal tissues and tissues with chronic inflammatory conditions were collected and compared. A number of MIR spectral bands were identified as diagnostic markers for chronic inflammatory vascular conditions such as vulnerable plaques seen with atherosclerotic disease. These markers were used to develop a catheter-based diagnostic method and apparatus which use the broad-band MIR light or marker bands of MIR laser light for detecting and imaging disease tissues, particularly vulnerable lesions and other vascular diseases.

2. Related Art

Atherosclerosis is a common form of cardiovascular disease that leads to insufficient blood supply to critical body organs, resulting in heart attack, stroke, and kidney failure (Libby, P. *Scientific American* 2002, 286, 47-55). Atherosclerosis can also cause major complications in those suffering from hypertension and diabetes, as well as tobacco smokers. It is known that this form of the cardiovascular disease is the leading cause of death and disability in the developed world. In the United States alone, atherosclerosis is responsible for almost one million fatalities each year, which is more than one half of all deaths. In addition, almost 5 million persons are afflicted with cardiovascular disease and require hospitalization for corrective surgery each year. Among those receiving corrective surgery, almost one half would suffer in less than six months the recurrence of stenosis (an accelerated form of atherosclerosis or artery stricture) and even sudden cardiac deaths (Ross, R. *Nature* 1993, 362, 801-809), particularly in young men (Naghavi, M.; Madjid, M.; Khan, M. R.; Mohammadi, R. M.; Willerson, J. T.; Casscells, S. W. 2002, 30).

Such failure of coronary angiography in determining the clinical severity and in predicting future recurrence of acute coronary syndromes in symptomatic patients has driven scientists to develop new diagnostic methods for identifying vulnerable atherosclerotic plaques. Among them are the following promising technologies: contrast enhanced and intravascular magnetic resonance imaging (MRI), optical coherence tomography (OCT), electron-beam computed tomography (EBCT), angioscopy, elastography, intravascular ultrasound (IVUS), and fluorescence spectroscopy. With the exception of fluorescence spectroscopy (to some extend), these new methods aim at plaque structure/morphology or plaque activity/physiology; although there is overwhelming evidence that atherosclerotic plaques are not merely an accumulation of fat in the arterial wall. Medical research conducted (Chan, A. W.; Ross, J. *Clinical & Investigative Medicine—Medecine Clinique et Experimentale* 1997, 20, 320-326; Kaneko, E. et al., *Coronary Artery Disease* 2000, 11, 599-606; Forte, A. et al., A. *Journal of Cellular Physiology* 2001, 186, 307-313) and clinical observations (Davies, M. J.; Thomas, T. *Philos Trans R Soc Lond Biol Sci* 1981, 294, 225-229; Walts, A. E.; Fishbein, M. C.; Sustaita, H.; Matgloff, J. M. *Circulation* 1982, 65, 197-201; Falk, E. *Br Heart J* 1983, 50, 127-134) acquired in the past decade have revealed that atherosclerosis is indeed not a simple fat buildup at the arterial wall. Instead, it is an ongoing active disease caused by progressing atherosclerotic/vulnerable plaques, which are an evolving active collection of different migrated, proliferated, infiltrated cells (mainly smooth muscle cells and immune cells especially inflammatory macrophages), apoptotic/narcotic cells, along with one or more immune-triggering agents such as oxidized LDL and even infectious agents.

The most critical information needed for the accurate determination the clinical severity and reliable prediction of future recurrence of acute coronary syndromes in symptomatic patients is the microanatomic characteristics of plaque composition. A more promising in vivo diagnostic tool for preventive cardiology should be a method that enable an accurate identification and characterization in coronary patients of the plaques that are vulnerable to rupture in the future, i.e. "vulnerable plaque."

Others in the art have recently attempted to provide Raman-based devices and techniques for diagnoses of tissues. Raman-based devices and techniques involve irradiating the tissue with light in the visible or near-infrared (NIR) regions of the electromagnetic spectrum, detecting light re-emitted (only about one per $10^7$ incoming photons) by the tissue at the same frequency, or within a range of frequencies on one or both sides of the irradiating light, and determine the Raman shifted frequencies in the MIR region to diagnose the tissue's chemical conditions. An apparatus for the spectroscopic diagnosis of tissue conditions is described in Rava et al., in U.S. Pat. No. 6,697,665, and is hereby incorporated by reference. Richards-Kortum et al., in U.S. Pat. No. 6,095,982, describe methods and apparatus for detecting tissue abnormality through fluorescence or Raman spectroscopy after excitation of tissues in NIR wavelengths, and is also hereby incorporated by reference. Gellermann et al., in U.S. Pat. No. 6,205,354, described method and apparatus for the determination of levels of carotenoids and similar chemical compounds in biological tissue such as living skin.

Unlike the present invention, these Raman spectroscopy methods and apparatus are less sensitive to biomolecules with polar bonds and functional groups, which can be important during inflammation or in disease tissues. They also rely on the low intensity of re-emitting light (about one per $10^7$ incoming photons) by the tissues, and often suffer interferences from background autofluorescence signals from tissues.

BRIEF SUMMARY OF THE INVENTION

The present invention relates to methods and apparatus that exploit the drastic changes in the optical properties in tissues in the mid-infrared region of the electromagnetic spectrum because of the pathophysiologically induced changes in the chemistry and structures of tissues. The invention comprises an optical method of detecting pathogenesis in tissues, and of characterizing the pathophysiologic molecular and structural features of disease states within vascular systems or other body compartments using mid-infrared (MIR) reflectance and reflectance generated absorption spectroscopy. The pathophysiologic features of disease states in tissues can be observed by increases in reflectance and in the numbers of reflectance generated absorbance peaks in the range of wavenumbers 4000 to 400 $cm^{-1}$.

In one embodiment, the present invention involves first using a broad-band photon source that emits light in the mid-infrared (MIR) region and collecting reflectance spectrographs and reflectance generated absorption spectrographs of segments of normal tissues and tissues with chronic inflammatory conditions. Exemplary MIR spectral bands are herein identified and verified as diagnostic markers for chronic inflammatory vascular conditions such as vulnerable plaques which are associated with atherosclerotic disease. Many disease tissues contain reflective constitutents that absorb only part of the incident MIR light. Light that is bounced off by reflective constituents inside the tissue is collected and amplified and delivered to the computer for analysis. Reflected light measured at predetermined wavenumbers or bands of wavenumbers are used to generate a spectral signal pattern representative of the tissue conditions at the location of examination. Certain wavenumber regions are shown to be informative in characterizing the state of the pathophysiology of human disease and disorders including but not limited to atherosclerotic disease.

One object of the invention is to provide non-destructive in vivo devices, methods and procedures for identifying and characterizing normal and diseased tissues using mid-infrared reflectance spectroscopy and reflectance generated absorption spectroscopy.

Another object of the invention is to describe methods for measuring reflectance spectra and for identifying reflectance generated absorption spectral markers in in vivo tissues which are indicative of vascular, atherosclerotic or other diseases. Such physiologically derived spectral markers that are indicative of the presence of, and not limited to non-native or increased lipids, apoptotic or necrotic cells in a tissue, biomineralization (e.g., calcified deposits), infracted tissues, vulnerable plaques (VP), or inflammatory conditions. One object of the invention is to provide methods and applications to diagnose or detect coronary atherosclerotic heart disease.

The invention provides a catheter-based method of characterizing conditions in a tissue, comprising (a) providing light in selected wavenumbers within the range of mid-IR spectrum; (b) directing the light to an area of tissue at a location; (c) collecting light reflected from the location and generating a reflectance spectra; and (d) comparing said reflectance spectra to a reference spectra of normal tissue, whereby a location having an increased number of absorbance peaks at selected wavenumbers indicates a tissue containing a physiological marker. The step of providing light comprises the use of a mid-infrared source and directing the light into the blood vessel of a test subject. In a preferred embodiment, the light is delivered to the blood vessel of a test subject via a catheter having an optical probe.

Increased numbers of absorbance peaks can be observed in reflectance spectra and reflectance generated spectra is in the range of wavenumbers 4000 to 400 $cm^{-1}$. In some embodiments, the increased numbers of absorbance peaks are within at least one range of mid-infrared wavenumbers selected from the group of: ~3500-3000, ~3020-3000, ~2950-2800, ~1800-1450, ~1710-1760, ~1690-1610, ~1520-1500, ~1480-1450, ~1100-900 and ~900-400 $cm^{-1}$. In certain embodiments, the increased numbers of absorbance peaks are in the range between ~3000-3100 $cm^{-1}$ and between ~1710-1760 $cm^{-1}$. In a preferred embodiment, the presence of said physiological marker in said tissue is an indicator of disease tissue.

The catheter-based method can furter comprise the step of generating a spatially resolved map of reflectance generated spectral signals from different locations within a tissue or the blood vessel or aorta of the test subject.

The invention further provides an apparatus for characterizing tissue conditions, comprising: (a) a single or multiple source of mid-IR light covering a range of mid-infrared wavenumbers; (b) a catheter coupled to said source and a detector or an array of detectors to detect light reflected by a tissue; and (c) a computer means for generating the reflectance generated spectra at selected wavenumbers detected by said detectors.

In one embodiment, the computer means has stored therein the reference wavenumber range of 4000-400 $cm^{-1}$. In a preferred embodiment, the computer means has stored therein the following reference wavenumber ranges, expressed in $cm^{-1}$: ~4000-2800, ~3500-3000, ~3020-3000, ~2950-2800, ~1760-1710, ~1690-1610, ~1520-1500, ~1480-1450, and ~1100-900 and ~900-400.

In another embodiment, the catheter comprises a source fiber and a detection fiber having a tip or tip array. The catheter can be inserted into the lumen of a patient's blood vessel, artery or other tissues suspected of containing physiological markers indicative of vascular disease or other inflammatory conditions.

In some embodiments, the apparatus can optionally comprise an interferometer. In another embodiment, the apparatus can be further comprised of a tuning system for the source, a cooling means for the detector, or the additional use of customized bandwidth and special gain for DC- and/or AC-coupled preamps for the detectors to increase the signal-to-noise ratio of the detectors.

The invention also provides a method of characterizing atherosclerotic plaque of blood vessels, comprising the steps of: (a) providing light in selected mid-IR wavenumbers between about 3800 to about 2800 $cm^{-1}$; (b) directing the light through a probe to an area on a blood vessel or aorta; (c) measuring reflected light returning through the probe over a range of said wavenumbers to generate a pattern of spectral signals representative of said area; and (d) comparing spectral signals from a reference spectra to the spectral signals from said area, whereby an having atherosclerotic plaque has enhanced reflectance and increased spectral features.

The invention also provides a method of characterizing a biological material that has enhanced reflectance and/or spectral features, comprising the steps of: (a) providing light in selected mid-IR wavenumbers between about 4000 to about 400 $cm^{-1}$; (b) directing the light through a probe to an area of said biological material; (c) measuring reflected light returning through the probe over a range of said wavenumbers to generate a pattern of spectral signals representative of said area; and (d) comparing spectral signals from a reference spectra to the spectral signals from said area for enhanced reflectance and/or spectral features.

In one embodiment, light is provided in mid-IR wavenumbers between about 3800 to about 2800 $cm^{-1}$, whereby an area of the biological material having enhanced reflectance and increased spectral features is indicative of an atherosclerotic plaque.

In another embodiment, light is provided in at least one range of selected mid-IR wavenumbers selected from the group of: ~3020-2800 $cm^{-1}$, ~1760-1710 $cm^{-1}$, ~1450-1460 $cm^{-1}$, and ~1200-900 $cm^{-1}$, whereby an area of the biological material having enhanced reflectance and increased spectral features is indicative of the presence of non-native lipids.

In another embodiment, light is provided in at least one range of selected mid-IR wavenumbers selected from the group of ~1740-1400, ~1100-900 and ~900-400 $cm^{-1}$, whereby an area of the biological material having enhanced reflectance and increased spectral features is indicative of inflammatory conditions.

In another embodiment, light is provided at selected mid-IR wavenumbers between about 1740-1700 $cm^{-1}$, whereby an area of said biological material having enhanced reflectance and increased spectral peaks are indicative of increased numbers of leukocytes, lymphocytes and macrophages.

In another embodiment, light is provided selected mid-IR wavenumbers are between about 1100-900 $cm^{-1}$, wherein enhanced reflectance and increased spectral peaks at about 1090, 1052, or 965 are indicative of lymphocytes and macrophages thereby indicating an inflammatory condition of accumulations of leukocytes, specifically lymphocytes and macrophages. In yet another embodiment, all three ranges of selected mid-IR wavenumbers is provided and measured.

In another embodiment, light is provided at selected mid-IR wavenumbers between about ~1690-1610 $cm^{-1}$, whereby an area of said biological material having enhanced reflectance and increased spectral peaks at ~1620 $cm^{-1}$ and ~1678 $cm^{-1}$ is indicative of accumulation of dead (apoptotic and/or necrotic) cells in a tissue.

In another embodiment, the invention provides for a method of spectroscopic diagnosis of tissue comprising: (a) irradiating a subsurface portion of tissue at a target area with radiation having a frequency within the mid-infrared range, transmitted through a fiber optic cable; (b) detecting light reflected by the area of tissue in response to the radiation, the light having a range of 4000 $cm^{-1}$ to 400 $cm^{-1}$; and (c) analyzing the detected reflectance light to diagnose the tissue including the step of comparing the detected light with reference data.

In one embodiment, in the detection step the reflected light is collected through the fiber optic cable. In another embodiment, in the irradiation step a catheter means is provided for insertion of the fiber optic cable in body lumens. The fiber optic cable receives light reflected by the tissue and transmits the reflected light to a spectroscopic analysis system. In another embodiment, an alternate spectrophotometer can be used to receive the reflected light. In another embodiment, the method can further comprise a step of rotating the fiber optic cable radially within the body lumens, whereby data is acquired at various target locations radially within the lumen. The step of radial acquisition of data can be repeated thereby performing a 360-degree spectral analysis of the body lumens.

In another embodiment, a method of characterizing conditions in a tissue, comprising the steps of: delivering mid-infrared bright light to a tissue to be diagnosed, irradiating said tissue with said bright light, detecting light reflected by the tissue within the same range of MIR frequencies, and determining the chemical composition and cellular conditions in the tissue.

DETAILED DESCRIPTION OF THE PREFERRED EMBODIMENT

Introduction and Methods

The present invention relates to methods and systems of performing reflective MIR spectroscopic diagnosis of disease tissues. The presence of highly reflective crystalline and other fine-structure components in disease tissues, and the fact that many of these non-native materials contain very little water, have provided an opportunity to use the sensitive MIR reflectance and reflectance generated absorption spectroscopy to probe pathophysiological conditions in tissues in vivo. Unlike normal tissues that usually attenuate a large fraction, or even all of incoming MIR light, many constituents inside disease tissues including but not limited to atherosclerotic tissues are effective MIR reflectors that can transform the tissue into a highly reflective matrix. By analyzing the reflectance generated absorption spectral bands, one can readily characterize the conditions of the tissues. For atherosclerotic tissues, for example, the targets are the presence of unusual amount of lipids, cholesterol crystalline, calcified deposits, foam cells, apoptotic or necrotic cells, collagen, and nitrated protein.

The present invention utilizes in part MIR reflectance spectrographic technology in conjunction with MIR sources that are brighter than the conventional thermal MIR sources. The advantages of MIR spectrographic technology as described herein are: (1) MIR has minimum scattering and autofluorescence in biological samples; (2) MIR spectroscopy can provide a wealth of information that is molecule and structure specific (e.g., providing inherent chemical information about functional groups, including their types, interactions and orientation) with high sensitivity; (3) MIR spectroscopy can identify physiological states of cells (e.g., foam cells, blood cells, cells at different cell cycles, dying cells); and (4) it can be a qualitative and quantitative technique without the use of dyes or labeling chemicals. The advantages of a bright light source, especially those that can act as a coherent light source, are that it can penetrate deeper into biological tissues and biological fluid such as blood, and that it can increase signal-to-noise ratios in the MIR reflectance spectral measurements at individual cells as well as individual plaques.

Mid-Infrared Reflectance Generated Absorption Spectroscopy of Tissue Lesions

Biomineralization results in formation of non-native materials such as microcalcification, which is commonly found in disease tissues, such as benign and malignant lesions of breast tissues and atherosclerotic tissues. Non-native materials found in these disease tissues have very little water and are highly reflective to MIR light. Their presence in tissues converts the tissues into a MIR reflective matrix, thus providing an opportunity to use MIR reflectance and reflectance generated absorption spectroscopy to sensitively probe pathophysiological conditions in tissues. The tissues can be examined ex situ, ex vivo, in vivo.

Figure 1A:
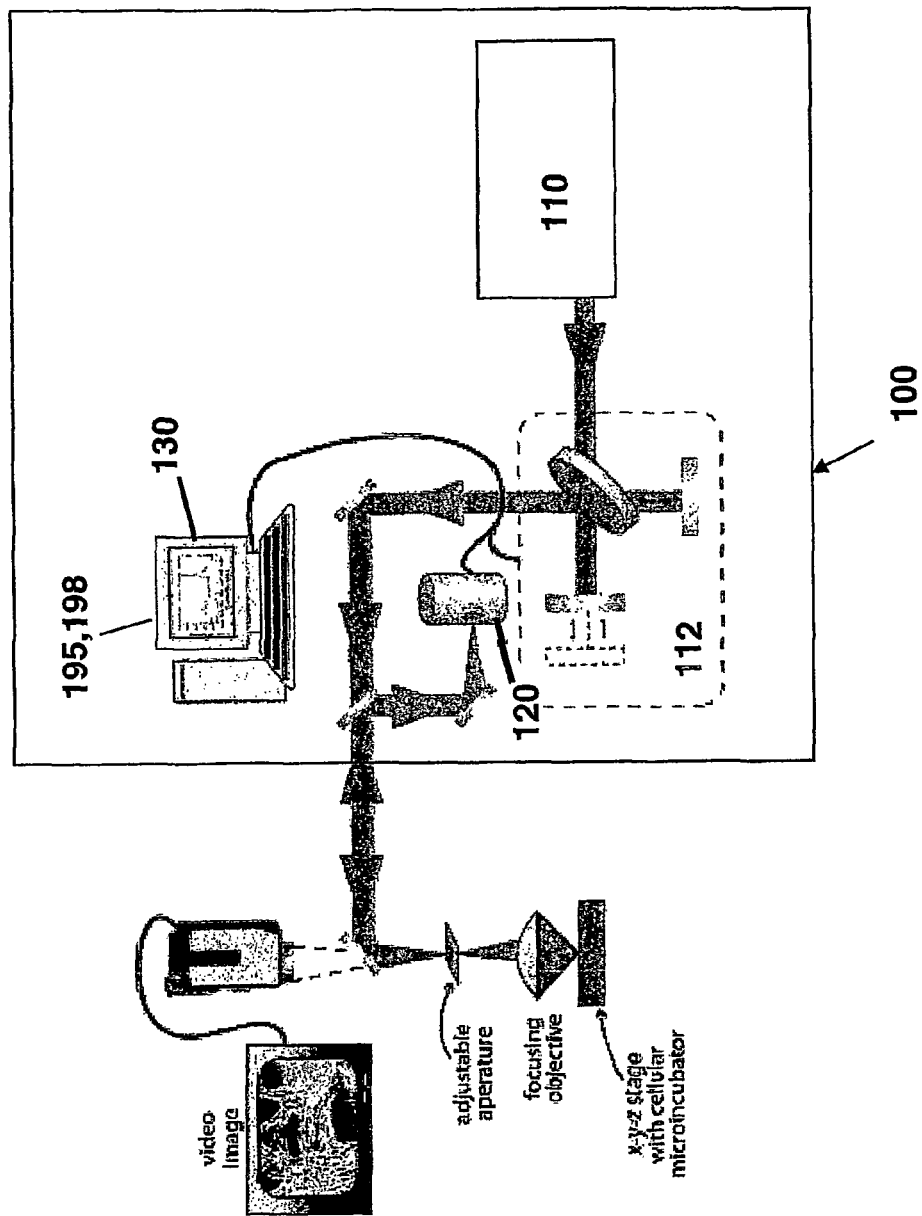
FIG. 1A is a schematic showing one embodiment for a system to measure the MIR reflectance generated spectra of a tissue suspected of having lesions or diseased portions.

FIG. 1A schematically illustrates a preferred embodiment of the device 100 to measure the MIR reflectance generated spectra of a tissue suspected of having lesions or diseased portions. In one embodiment, a device as described and shown in Hoi-Ying N. Holman, Michael C. Martin, and Wayne R. McKinney, "Tracking chemical changes in a live cell: Biomedical Applications of SR-FTIR Spectromicroscopy," *Proceedings of the First International Conference on Biomedical Spectroscopy*, Cardiff, Wales, Jul. 7-10, 2002. Spectroscopy—An International Journal 17(2-3), 139-159 (2003). LBNL-51337, can be used. Generally the device 100 comprises a mid-IR light source 110, a detector 120 connected to a computer means 130. The IR light source 110 also can be optically connected to an optional diffusive reflectance spectroscopy interferometer or a Fourier transform infrared (FTIR) bench with a Michelson interferometer 112. The source 110 emits mid-infrared light 130 at the loci of the tissue sample spot 140 to be interrogated. The arrows in the schematic show the direction of the light 140. The detector 120 detects the reflectance generated light after it has been reflected and absorbed by the tissue sample 140 and transmits the signal to the computer means 190.

A computer or other means 190 stores the spectral information which is a spectrograph of light intensity versus wavenumber or wavelength. This spectral information can be displayed immediately on an output display means 195, compared with reference spectra stored in the computer, displayed on the differential spectral display 198 and analyzed. Such analysis and comparison will provide a quantitative image of the distribution of lesions in the tissue. The computer 190 may have stored therein spectral characteristics of the mid-infrared reference wavenumber segments expressed in units of $cm^{-1}$. Having stored spectral characteristics in these segments and reference numbers allows the device to generate a pre-interpreted output.

Analysis and interpretation of MIR reflectance generated absorption spectroscopy of tissues involves measuring the reflectance of incident MIR radiation as a function of photon energy, and mathematically converting to absorbance as a function of photon energy. Mid-infrared radiation is in the region of the electromagnetic spectrum which is bound by the near infrared (NIR) region at high frequencies and the far infrared (FIR) region at low frequencies. The present technique focuses on the application of reflectance from tissues of molecular and structural features from the MIR region of the electromagnetic spectrum because of its wealth of chemical information with exceedingly high sensitivity.

The energy (E) of MIR photons may range from 0.5 to 0.05 eV, or in terms of wavelengths ($\lambda$) from 2.5 to 25 µm, or the wavenumbers ($\nu$) range from roughly 4000 to 400 $cm^{-1}$. At present, a wavenumber defines the number of waves per unit length. The term, "wavenumber" is used herein to mean $1/\lambda$ where $\lambda$ is the wavelength. Wavenumbers and wavelengths can be inter-converted using the following equation:

$$\nu(\text{in cm}^{-1}) = (1 \times 10^4)/\lambda(\text{in µm}) \tag{I}$$

Wavenumbers and energy can also be inter-converted using the following equation:

$$\nu(\text{in cm}^{-1}) \sim 8100 \times E \text{ (in eV)} \tag{II}$$

Thus, wavenumbers are directly proportional to the energy associated with the photon, and inversely proportional to the wavelength. The wavenumber unit ($cm^{-1}$, reciprocal centimeter) is more commonly used in modern infrared instruments that are linear in the $cm^{-1}$ scale. At present, the recommended unit of wavelength is µm micrometers, but µ (micron) is used in some older literature.

When MIR photons enter healthy tissues, most photons are attenuated inside the tissue and very little are reflected. However, when MIR photons enter disease tissues such as atherosclerotic or inflammatory tissues, some MIR photons are "reflected" or in other words, bounced off and redirected by non-native constituents inside the disease tissue. Thus, the term "reflectance" as used herein, is meant the measurement of the photons reflected and redirected by non-native constituents in a tissue. The photons can then measured at each mid-infrared wavelength. By defining "reflectance" as used herein, R, as the ratio of the detected light intensity I to the incident light intensity $I_o$, one can express reflectance (R) in terms of absorbance (A) as the logarithm to the base 10 of the reciprocal of the reflectance (R).

$$A = \log_{10}(1/R) = -\log_{10} R = -\log_{10}(I/I_o) \tag{III}$$

This equation holds for each single wavenumber through out the entire MIR spectrum By measuring the reflectance of mid-infrared photons over a series of wavelengths, it is possible to obtain absorption information via equation (III). Infrared absorption occurs only when the frequency of the incident infrared photon matches exactly the molecular vibration frequency which produces an oscillating dipole moment perpendicular to the plane of incident This selective absorption makes infrared spectroscopy a powerful means of studying the composition and structure of biological samples.

The data transformation process described above allows one to compare the band characteristics of a reflectance generated absorption spectrum with those in a MIR absorption database, such as those available in the art This comparison provides an opportunity to identify and measure the presence of a certain function group or even a certain type of biomolecules found in a disease tissue.

In one embodiment, data is displayed both in the form of reflectance and of reflectance generated absorbance. Infrared absorption information is generally presented in the form of a spectrum with wavenumber or wavelength as the x-axis, and percent reflectance or absorbance as the y-axis. Reflectance spectra provide better contrast between intensities of strong and weak bands because reflectance ranges from 0 to 100% whereas absorbance ranges from infinity to zero. The same sample will give quite different profiles for the infrared spectrum, which is linear in a wavenumber. It will appear as if some infrared bands have been contracted or expanded.

In studying spectra of disease tissues, one may notice from spectral peak shape that MIR reflection measured may be a combination of specular reflection and diffusion reflection, depending on the incident angle(s) of the beam and the local surface roughness of the tissue in comparison to the wavelength of the MIR photons. Issues of specular reflectance can be addressed in various ways, including by varying the angles of incidence, by applying Kramers-Kronig transformation to pre-process the reflectance data, or by building a spectral library of specular reflection of tissues. Such a library will enable the identification of the presence of specular reflection, accelerating data processing and analysis.

Absorption spectra are obtained from reflectance measurements via equation (III), which may be incorporated in software or algorithms used on the computer means 190 for analysis. While looking at tissues with plaques, one may notice from spectral peak shape that MIR reflection in a certain range of wavenumbers may be dominated by specular reflection or a combination of specular and diffusion reflection. Specular reflectance spectra possess derivative-shape bands, and are distinctly different from diffusion reflection spectra. To process the reflectance data in the spectral region wherein specular reflection dominates, processes such as Kramers-Kronig transformation can be used. A spectral library of specular reflection of aorta tissues of different disease states also can be built to help accelerating the data processing and analysis. The final outputs are spectra that are often closed to the conventional absorption spectra.

Figure 4:
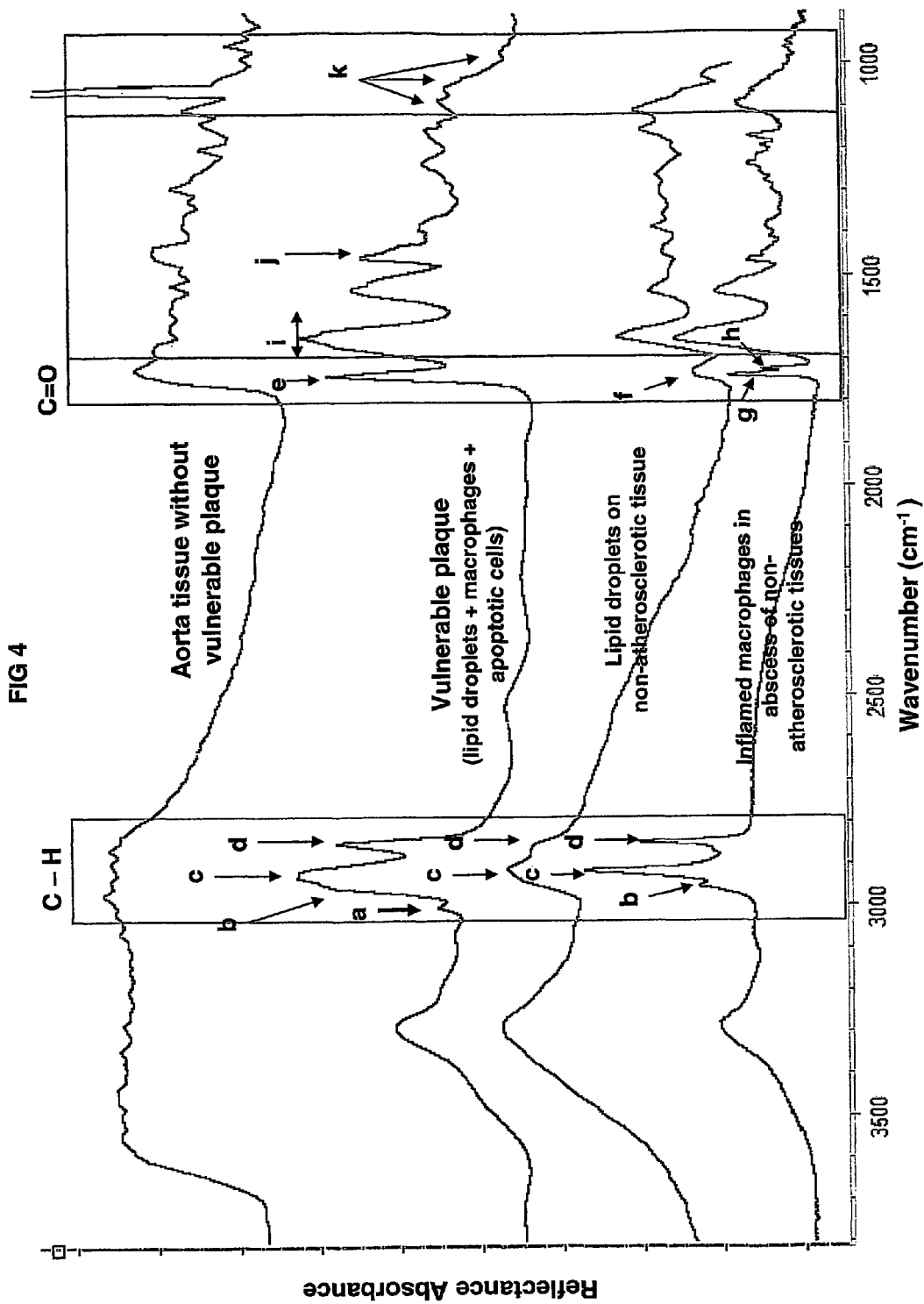
FIG. 4. summarizes reflectance generated absorption spectrographs showing data from (a) an aorta tissue free of VP, (b) an aorta tissue of VP, (c) a non-atherosclerotic tissue with lipids droplets, and (d) macrophages in an abscess of non-atherosclerotic tissues.

Analysis of reflectance generated absorption spectra can be further carried out by observing the spectral features, changes and characteristics (e.g., peak position, peak height, bandwidth) of multiple bands within defined wavenumber regions or "marker segments" on spectrographs such as those shown in the boxed regions in the FIG. 4. By observing spectral features in these marker segments in the MIR region, the presence of various physiological markers and features can be detected, including the presence, absence or changes in specific types of tissues, cells, proteins, lipid compositions and structures, biomineralization, or other biomolecules. By the term, "spectral features" it is intended to include features such as unique peaks, single or multiple peaks, broad peaks and envelopes that are typically observed in spectroscopy, and is used interchangeably with descriptions of such features.

According to the method, physiological markers can be identified by unique MIR features within MIR marker segments to indicate the presence of absence of plaques prone to rupture (i.e. vulnerable plaque). No dyes, contrasting agents, or labeling compounds are necessary for the reflectance measurements to differentiate tissues with plaques from tissues that are free of plaques. The unique composition and structure associated with vulnerable plaques (VP) have made VP a natural amplifier for diagnosing atherosclerosis by means of reflective absorption spectroscopy.

Figure 3:
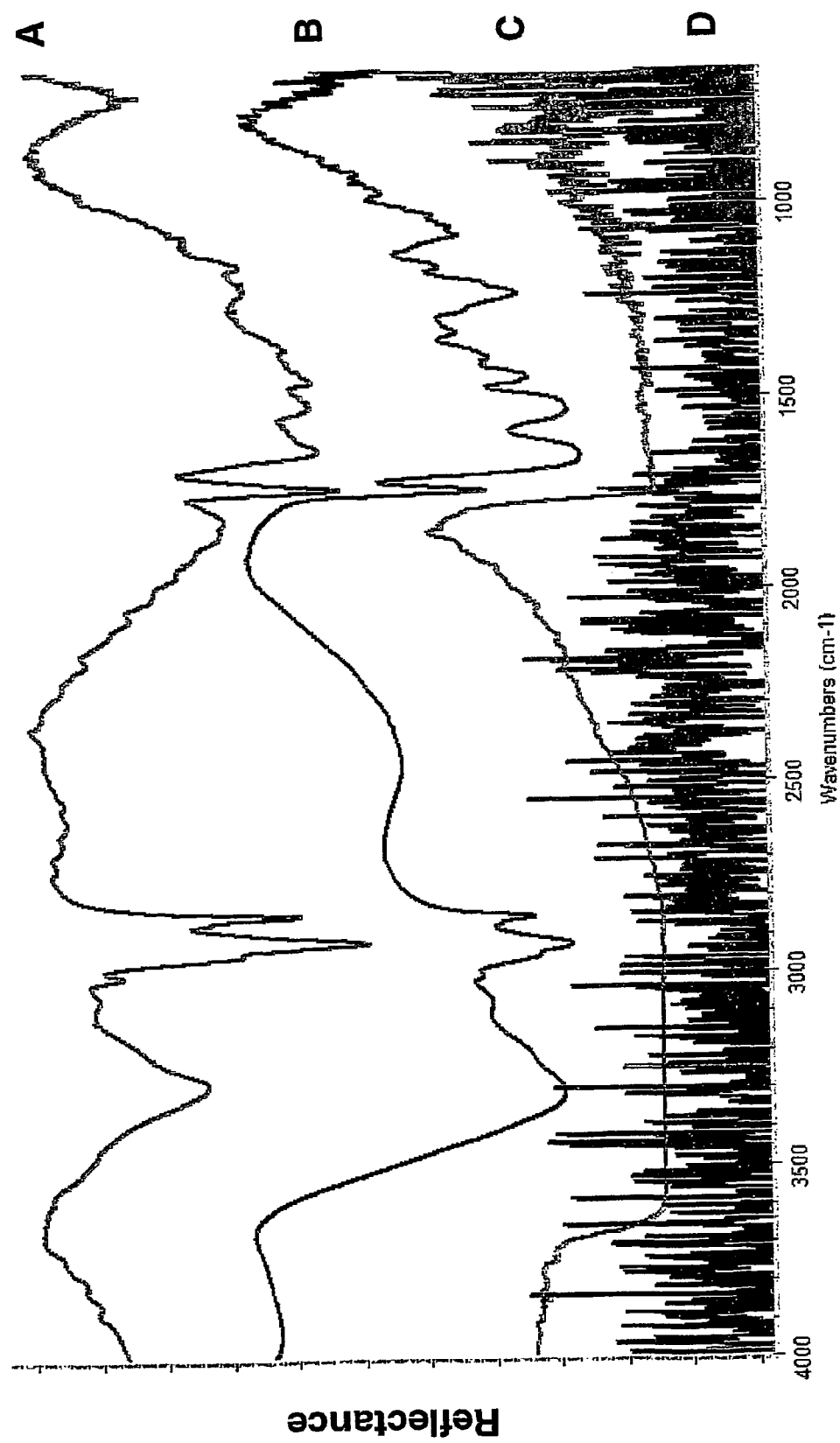
FIG. 3. compares reflectance spectrographs of aorta tissue (a,b) having vulnerable plaques and (c,d) without vulnerable plaques.

Furthermore, the present method can detect the presence of physiological atherosclerotic markers such as LDL, oxidized LDL, foam cells, infiltrated inflammatory cells, biomineralization, and excessive cell death such as apoptotic/necrotic cells. As shown in FIGS. 3 and 4, the present method can also detect markers and features of apoptotic and necrotic cells, including but not limited to, activated macrophages, inflamed macrophages, and foam cells; the presence of nitrated protein; biomineralization; changes in the nature of lipid compositions and structures, such as cholesterols, high density lipids (HDL), low density lipids (LDL) and oxidized low density lipids (oxLDL); the presence of infarcted tissues (modification of the extracellular matrix following myocardial infarction; denatured/aggregated proteins) and normal aortic tissue; and other physiological markers correlated with plaques prone to rupture (i.e. vulnerable plaques).

Using the method to study sites of inflammation, one can also observe increased numbers of absorbance peaks is in the range of wavenumbers 4000 to 400 cm$^{-1}$. Specfic wavenumber regions and ranges can be selected to interrogate a tissues. For example, different spectral features may arise in marker segments between wavenumbers 3500 and 2800 and between 1800 and 900 cm$^{-1}$, a smaller range of wavenumbers can be "selected" to interrogate a tissue. In certain embodiments, spectral features were found to be observed at the following reference wavenumber segments expressed in units of cm$^{-1}$: 4000-800, 3800-2800, 3050-2800, 1800-1000, 1760-1710, 1700-1610, 1600-1500, 1520-1500, 1480-1450, 1100-900 and 900-800 cm$^{-1}$.

The following marker segments are exemplary of the types of marker segments that can be characterized by the unique peaks or spectral features associated with those from disease tissues as compared to reference spectra from normal tissues. These unique MIR reflectance generated absorbance peaks in the spectral tracing generally correspond well with those obtained from MIR transmittance generated absorbance peaks that are indicative of excised specimens having vulnerable plaques. Reflective absorption spectral peaks observed at these wavenumbers may be associated with relevant chemical or biological conditions associated with a blood vessel as described herein and summarized in Table 1 below.

TABLE 1

Examples of MIR reflectance generated absorption markers for characterization and/or identification of vulnerable plaques. These markers were obtained by using the apparatus and method described in this invention

| Approximate Band position in cm$^{-1}$ | Assignment | Associated features in vulnerable plaques |
| --- | --- | --- |
| ~3800-3000 (centered at ~3300) | Hydroxyl peaks [vOH stretching] | Features: A decrease in absorption intensity in this region. Causes: Structural proteins (e.g., elastin) in the arterial wall are prone to calcification during the process of atherosclerosis. Protein calcification is known to involve a significant lost of hydroxyl content because of the participation of the hydroxyl group of proteins in calcium coordination to form aggregated species (Vyavahare et al. 1999). |

TABLE 1-continued

Examples of MIR reflectance generated absorption markers for characterization and/or identification of vulnerable plaques. These markers were obtained by using the apparatus and method described in this invention

| Approximate Band position in $cm^{-1}$ | Assignment | Associated features in vulnerable plaques |
|---|---|---|
| ~3005 | Stretching vibration of an olefinic=CH band of unsaturated lipid chains of cellular lipids including phosphatidylserines at the outer plasma membrane leaflet. | Features: The absorption intensity at ~3010 will increase. Causes: Atherosclerotic plaques have excess apoptotic cells which are known to increase their production in phosphatidylserines and the presence of externalized phosphatidylserines. |
| ~2950, ~2870 | Asymmetric and symmetric stretching vibration of $CH_3$ groups | Features: A decrease (relative to the absorption intensity for $CH_2$ groups) in absorption intensity. Causes: Vulnerable plaques are associated with high contents of collagen which has limited number of methyl containing side-chains. |
| ~2926, ~2852 | Asymmetric and symmetric stretching vibration of the lipid acyl $CH_2$ groups of fatty acids | Features: A drastic increase in absorption intensity. Causes: Vulnerable plaques have high contents of non-native lipids with large numbers of $CH_2$ groups. |
| ~1750-1720 | Stretching vibration of the lipid ester carbonyl (C=O) groups. The exact location depends on the local hydrogen-bonding environment with shifts of approximately 50 $cm^{-1}$. For example, the lipid C=O groups that are not hydrogen-bonded and do not interact with hydrogen bond donors, the peak positions tend to center at higher frequencies. Vibration peaks associated with hydrogen-bonded lipid C=O groups tend to center at lower frequencies. | Features: A very intense sharp peak arises from non-native lipids. The peak parameters can be used to determine the lipid constituents, morphology, and mobility in the plaque. Cause: High-content of non-native phospholipids and cholesterol esters with C=O groups exceedingly sensitive to the immediate hydrogen bonding environments in surrounding cellular/tissue environments. ~1747-1743: the lipid C=O groups are in a highly non-polar immediate environment (e.g., non-polar fatty acids); highly immobile. ~1740: Stretching of C=O groups for lipids with some polar constituents such as phosphates, sugar and amino groups. ~1735: Stretching of phospholipid C=O groups for simple lipids such as cholesterol esters; C=O groups are more hydrogen-bonded; mobile. ~1723: C=O groups in protonated environments |
| ~1690-1610 | Arising from C=O stretching of the peptide groups of proteins (Amide I). 1678, 1620: Aggregated or denatured proteins (dead cells) 1659, 1637: α-helix/β-sheet | Features: New peaks at ~1678, but mostly 1620. Causes: Protein aggregations are known to associate with myocardial infarction (cell death) found in vulnerable plaques. |
| ~1560-1520 | Arising from N—H bending vibration of the peptide groups of proteins (Amide II). Highly sensitive to the local environment of H in the N—H groups. Strong hydrogen bonds restrict the bending vibration and increasing the frequency. | Ratio of absorption intensity of Amide I to Amide II for red blood cells are similar to pure proteins (Chiriboga et al. 1998) |
| ~1515 | Tyrosine ring vibration band: Tyr-OH, ν(CC), σ(CH) | Nitrotyrosine → 1510; nitrotyrosine is generally associated with nitrated proteins, and is often found in vulnerable plaques. |
| ~1467 | Bending vibrations of the lipid acyl $CH_2$ groups | Features: Become very prominently strong and sharp peak(s) in vulnerable plaques Cause: Abundance of acyl $CH_2$ groups in non-native phospholipids and cholesterols. |
| ~1200-900 | Phosphate vibration region | Features: Become distinctive with mineralized tissues |

TABLE 1-continued

Examples of MIR reflectance generated absorption markers for characterization and/or identification of vulnerable plaques. These markers were obtained by using the apparatus and method described in this invention

| Approximate Band position in $cm^{-1}$ | Assignment | Associated features in vulnerable plaques |
|---|---|---|
| ~1090, ~1052, ~965 | Vibrations of the P—O and C—O groups of the sugar-phosphate backbone of DNA | Features: Pronounced peak for glycogen-poor cells such as lymphocytes and macrophages<br>Causes: Vulnerable plaques have abundance of macrophages |

All wavenumber regions and specific wavenumbers described herein and also presented in Table 1 are approximate, and are meant to include ±15 wavenumbers. This is also further indicated by the terms, "about" and "approximate" and by the symbol, "~", which are meant to indicate that the wavenumbers should include ±15 wavenumbers from the indicated wavenumber or wavenumber range.

FIG. 3. compares reflectance spectrographs of aorta tissue (a, b) with vulnerable plaques and (c, d) without vulnerable plaques. The spectrograph shows that normal aorta tissues hardly reflect the MIR photons and form a "silent" background spectrum either throughout the MIR region (trace c) or in the region of wavenumber 3600-2800 $cm^{-1}$ and the region of wavenumber 1800-1000 $cm^{-1}$ (trace d). However, in atherosclerotic tissues, detailed sharp peaks and features appear in these two spectral regions (trace a, b).

FIG. 4. illustrates a typical reflectance spectrum dominated by specular reflectance in the tissue of an atherosclerotic aorta. Shown are the traces for aorta tissue without vulnerable plaque; vulnerable plaques (lipid droplets, macrophages and apoptotic cells); lipid droplets on non-atherosclerotic tissue; inflamed macrophages in abscess of non-atherosclerotic tissues. Shown are boxed regions are marker segments where spectral features indicative of disease tissues containing non-native constituents can be found. The peaks pointed to by arrows indicate the types, kinds and unique peaks that can be found within these marker segments of disease tissues containing non-native constituents.

Figure 5:
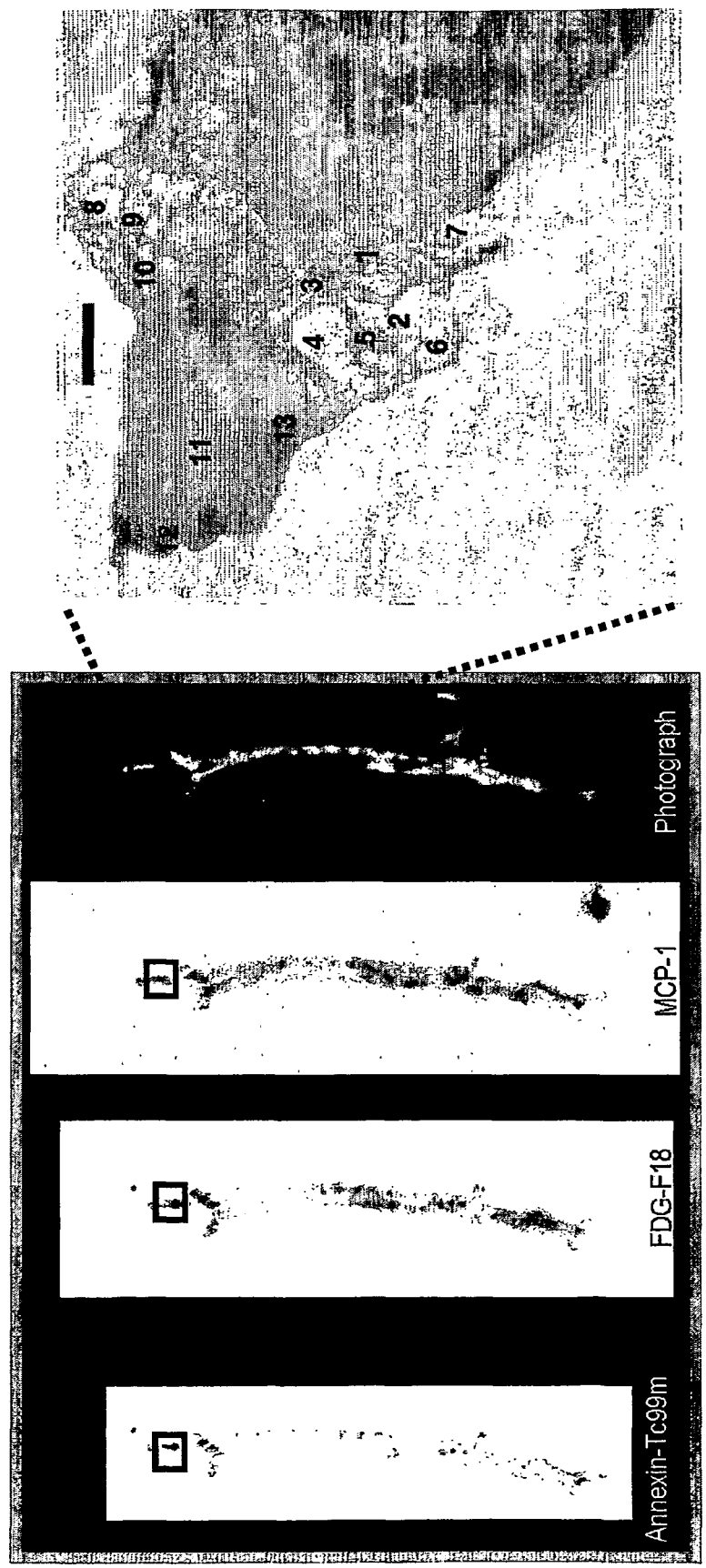
FIGS. 5A-5B are visible micrograph of a section of the aorta from an ApoE (−/−) mouse that has atherosclerotic plaques. Numbers on the micrograph in FIG. 5B indicate the locations of measurements. (The corresponding MIR reflectance generated absorption spectra measured at these sampling locations are shown in FIGS. 6-8, which demonstrate in details the uniqueness of the spectral fingerprints for vulnerable plaques.)

FIG. 5 is a summary graph of the MIR spectra of tissues of different inflammation conditions detected by the present method and apparatus and the different results that may be obtained. The Figure shows a spectrogram plotting wavenumber versus absorbance (as measured by reflectance generated absorption spectroscopy). Reflectance generated absorption spectra that have very broad and featureless "background absorption" are typical of normal aorta tissue observed in areas free of plaques.

Additional absorption peaks are seen in tissues with vulnerable plaque. In one embodiment, these peaks are generally in the region of wavenumbers 3100-2800 $cm^{-1}$, 1800-1700 $cm^{-1}$ (an area related to C═O groups) and 1600-1500 $cm^{-1}$, which arise from the vibrations of the lipid acyl —$CH_2$ groups, C═O stretching and from the N—H bending of the peptide groups in proteins and in other areas, such as ~1467 and ~1090 $cm^{-1}$, ~1050 $cm^{-1}$, and ~968 $cm^{-1}$ which may be assigned to the bending (scissoring) vibrations of the lipid acyl —$CH_2$ groups, and the C—C/C—O stretching vibration characteristics of the deoxyribose sugar moiety connected to phosphates in DNA. The locations of infrared absorption peaks of protein Amide I at ~1680 $cm^{-1}$ and ~1620 $cm^{-1}$ may arise from the presence of protein aggregations that are known to associate with myocardial infarction (cell death) found in vulnerable plaques.

In general, the fine fingerprints centered at approximately 2950 $cm^{-1}$ in the 3020-2800 $cm^{-1}$ region are considered highly diagnostic for vulnerable plaque, in that they are associated with the presence of numerous apoptotic cells (for example, a peak at ~3005 $cm^{-1}$, which is associated with the increasing production in phosphatidylserines and the presence of externalized phosphatidylserines) in addition to increases in collagen contents and non-native lipid pools having peak characteristics at ~2950, ~2926, ~2870, and ~2852 $cm^{-1}$.

Also, peaks arising from C═O groups at approximately 1760-1710 are highly significant in that the peak location and fine structure are very good indicators of the mobility, structure, and polarity of lipids as well as the protonated environment of the cells or tissues which are not found in normal or non-inflamed plaque.

Intravascular MIR Reflectance Generated Absorption Spectroscopy

In another embodiment, a non-destructive in vivo diagnostic method and procedure is provided for intravascular MIR (IMIR) reflectance and reflectance generated absorption spectroscopy.

In one embodiment, this method is used to diagnose atherosclerosis in vivo. Contrary to healthy tissues, atherosclerotic tissues contain non-native constituents including lipid droplets, cholesterol crystals and clefts, calcium hdyroxyapatite crystalines, foam cells. They have very little water, and at the same are known effective MIR reflectors. A fraction of the light that enters the atherosclerotic tissue bounces around beneath the tissue surface, is re-directed and leaves the tissue. This reflected light will be collected and analyzed for chemical composition and cellular conditions of the tissue.

The analysis of the IMIR reflectance spectra of the present method involves the identification of at least two different spectra: the generally non-descript features of normal aorta tissues without atherosclerotic plaques viewed over a continuum of MIR wavelengths, and the specific features of aortic atherosclerotic plaques (FIG. 3). The term "continuum" is considered herein as the "background reflectance generated absorption spectra" of normal tissues. The specific reflection generated absorption spectral markers are those that are correlated to the physiological, chemical and structural conditions of inflammation and modification of cellular matrix being studied. The specific reflectance generated absorption spectral features are superimposed onto the continuum.

Figure 1B:
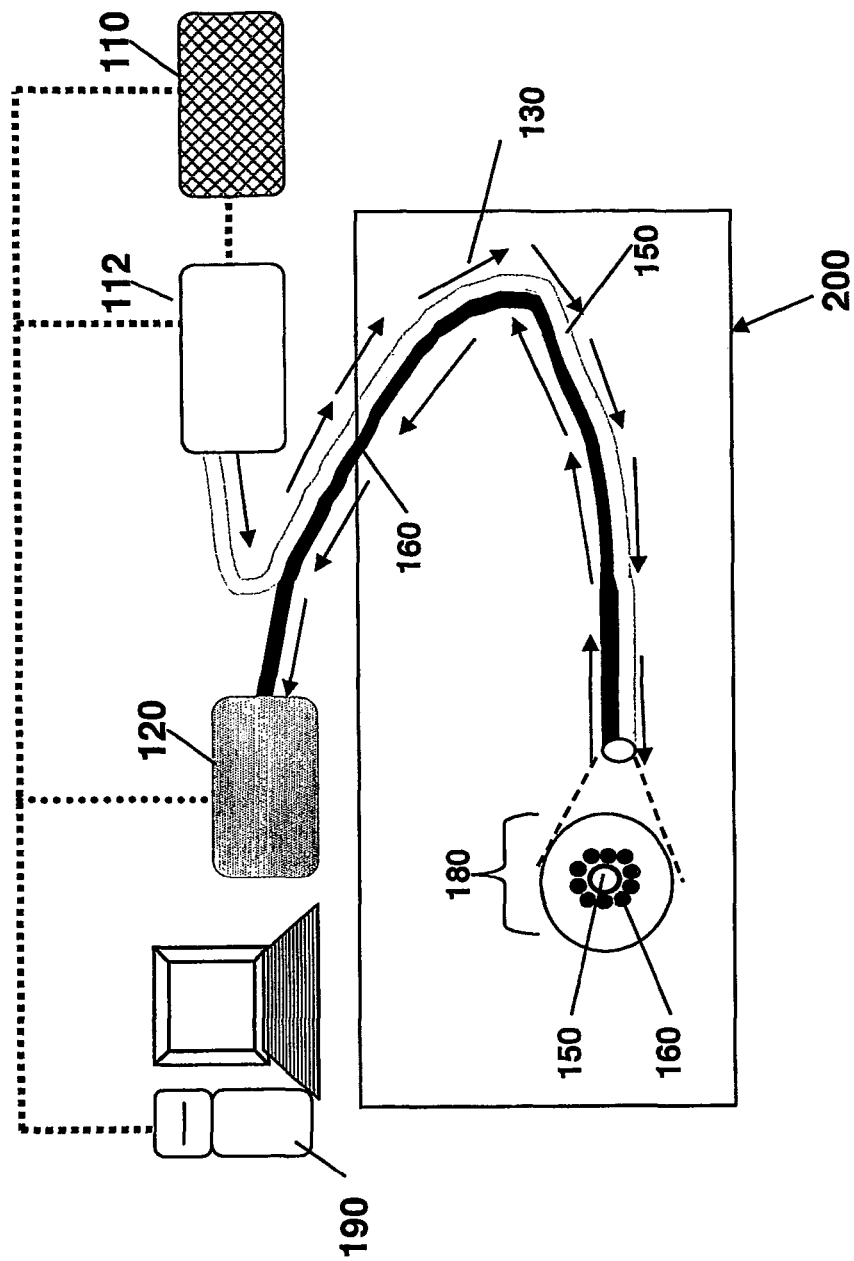
FIG. 1B is a diagrammatic illustration of one embodiment of a catheter-based system to be deployed in an artery or a body compartment of a test subject; note that the FTIR interferometer may or may not be needed.

In one embodiment, the present invention can be used to diagnose atherosclerosis in a living subject by means of a catheter passing through the subject's artery. A catheter-based diagnosis system in a preferred embodiment is illustrated in FIG. 1B and described below. Through the use of a catheter, a cardiovascular plaque can be subjected to comparative MIR reflectance generated absorption spectral analyses.

Figure 1C:
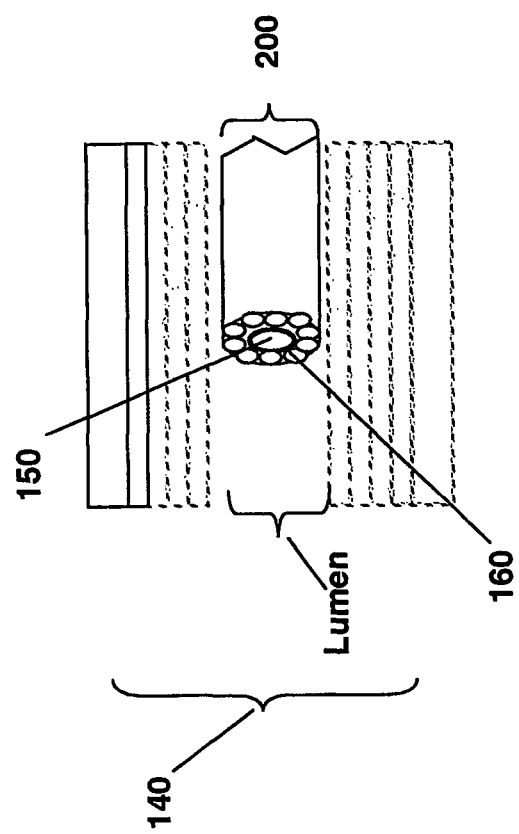
FIG. 1C is a schematic showing the distal end of the catheter inserted into the lumen of a vessel.

Referring to FIG. 1C, the light carrying catheter is introduced into the artery or tissue to be studied. A bright MIR light is delivered to the tissue to be interrogated through a source fiber. The light source can generate readings to a depth of up to hundreds of microns. The distal end of the catheter should be placed adjacent to or in contact with the arterial and vascular interrogation sites in the vessel or tissue. In FIG. 1C, an artery is illustrated, and the catheter is shown in physical contact with the surface of that artery. As is shown, the artery comprises several layers of muscle and epithelial tissue, and may or may not contain areas of plaque. Vulnerable plaques can usually be found within the first tens of microns below the tissue surface (tunica intima).

An in vivo sample studied by the IMIR spectroscopy method described herein is typically comprised of tissues suspected of having inflammatory cells, lipid pools and other immune triggering agents such as oxidized low density lipoproteins (OxLDL), cells that mediate an inflammatory/immune response, such as leukocytes, specifically macrophages or individual lesions. The lesions that can be studied include, but are not limited to, macrophages and/or lipids that are part of non-atherosclerotic inflammation (e.g., abscess) or atherosclerotic plaques. The teachings of the present invention may also be adapted for applications to other disease states involving the study of a lesion or inflammation, cell death, apoptosis and/or necrosis.

The MIR diagnosis of atherosclerotic tissues is not problematic even beneath a layer of blood. For example, if the atherosclerotic tissue to be diagnosed is an artery, the presence of blood in the vessel should not diminish the ability to detect reflectance generated spectra.

In one embodiment, this can be accomplished by using a very bright infrared source such as a free electron laser or a coherent laser. In another embodiment, one can limit the thickness of blood between the cell surface and the measurement system by employing an intra-aortic balloon catheter having a tip detector or tip array. The balloon can be inflated at the location of measurement to minimize the thickness of blood between the cell surface and the measurement system. In addition, if the data acquisition moments are synchronized with the heartbeat of a patient, the effect of blood will be minimized further. As the blood vessel contracts with each heartbeat, data is taken at that moment because the vessel contracts more tightly around the tip array of the catheter. It is also contemplated that a pressure-sensor may be present in the tip array to synchronize data acquisition with each contraction.

The presence of red blood cells is being observed if the ratio of the peak area centered at about 1650 cm$^{-1}$ to the peak area centered at 1545 cm$^{-1}$ is similar to the ratio detected in protein. Specifically this indicates that the probe tip is detecting blood cells, rather than the blood vessel endothelium. Thus in embodiments where detection of tissue or the epithelium is desired, it is important to keep the probe tip in direct contact with the surface to be studied.

The present method also provides MIR images of atherosclerosis in blood vessels such as an aorta. In one embodiment, the reflectance spectra is measured and mapped at various points along the blood vessel. In another embodiment, reflectance data is acquired at various points radially within a blood vessel, thereby performing a 360-degree spectral analysis.

It is contemplated that the present technique may optionally be used in conjunction with other known catheter-based diagnoses and treatments of cardiovascular diseases.

Apparatus and Experimental Set-up for IMIR

The present apparatus is built upon the experimental set up at the infrared beamline at the Advanced Light Source (ALS) at the Lawrence Berkeley National Laboratory, which may be adapted for a more commercial application, as described below and in the subsequent demonstration examples.

FIG. 1B illustrates a preferred embodiment for a catheter-based system using a broad-band light that provides photons with energy that span the entire mid-infrared region. The system includes the mid-infrared detection system 100 with broad-band light source 110, detector 120 and a computer 190, optionally connected to an interferometer 112. The source fiber 150 and detector fiber 160 are coupled within a catheter 200 having the detector tip 180. The light source 110 emits coherent MIR light, which is directed into an interferometer 112 to be modulated, and then passed to the catheter 200 that can be introduced into a subject. For example, the catheter 200 can be inserted through a vascular system to a body area for diagnosis. The modulated light that exits the interferometer 112 is delivered to a precise location via the optical fiber 150 inside the catheter 200.

The light exits the source fiber 150 and enters the tissue. In one embodiment, the light enters the tissue at a specified incident angle chosen by varying the angles of an incidence selector. An appropriate selection of angle(s) of choice provides measurements that allows for the identification and separation of specular reflection during data analysis. In one embodiment, the catheter fiber optic system has the option to rotate 360° and thus provide a 360° spectroscopic viewing of a vessel such as aorta.

The present invention is particularly adapted for directly measuring MIR-light being reflected, rather than being absorbed or transmitted. Thus, absorbance is generated by analyses of the reflected light from the tissues. Normal tissues reflect very little of the MIR light that penetrates the tissues. However, disease tissues such as atherosclerotic tissues contain highly reflective constituents. Light that enters the tissues is "bounced" around beneath the tissue surface by these reflective constituents and absorbed in part before redirected and leaving the tissue surface for collection. Referring to FIG. 1B, the direction of light is shown schematically by the arrows 130. The reflected light returned to the detector fibers 160, is amplified and detected by a detector or an array of detectors 120.

A computer or other means 190 stores the spectral information which is a spectrograph of light intensity versus wave-number or wavelength. In one embodiment, the computer 190 has software packages that can produce from this spectral information, reflectance spectra or reflectance generated absorption spectra at each location of interest the aorta. This spectral information can be displayed immediately on a output display means 195, and compared with reference spectra stored in the computer and displayed on the differential spectral display 198. Spatial displays of results from the comparison will provide a quantitative image of the distribution of lesions in the tissue.

The computer 190 may have stored therein spectral characteristics of the mid-infrared reference wavenumber segments expressed in units of cm$^{-1}$. Having stored spectral characteristics in specific wavenumber segments and reference numbers allows the computer 190 to generate a pre-interpreted output.

In another embodiment, a system uses a narrow-band light source such as a laser source similar to that shown in FIG. 1B, but without the use of an interferometer. In one embodiment the laser source 110 has built-in pulse-duration and power-level controls. By suitable design, one can customize the choice of power delivered, pulse duration, frequency, and even the width of the beam. Similarly, light is delivered to a precise location via the source fiber 150 inside the catheter 200.

Core Instrumentation

Figure 2:
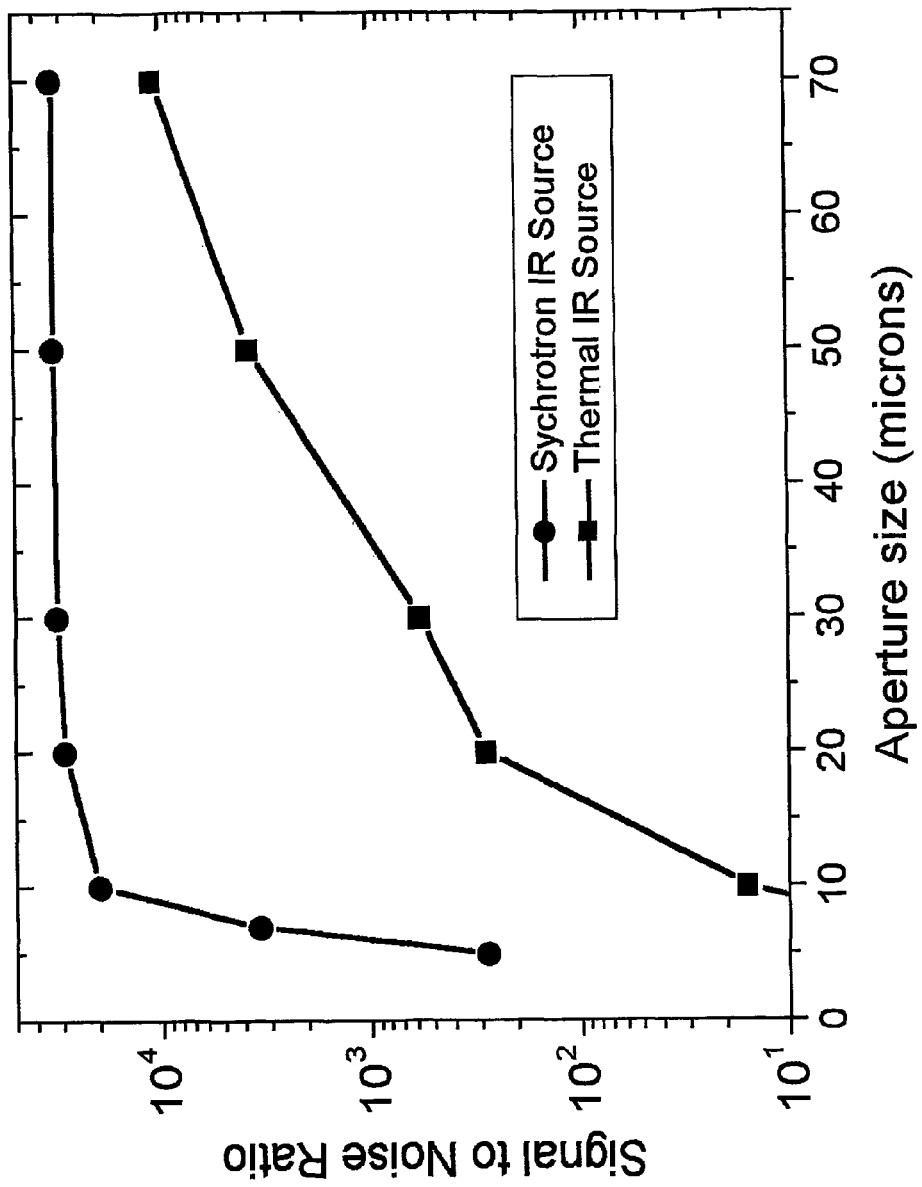
FIG. 2 is a graph demonstrating the motivation of using a bright and coherent light source instead of the conventional thermal source. The signal-to-noise ratios (SNR) increase significantly with the use of a bright source.

The present invention can be performed on a system using a bright light source 110 that acts as a coherent light source and emits photons in the mid-infrared range of the electromagnetic spectrum. The source can be broad-band or narrow-band, and preferably to be at least 100 times brighter than a conventional thermal source for infrared spectroscopy. The light source may be a synchrotron radiation-based source, a free electron laser (FEL), a laser, or other sources, preferably but not limited to one that can act as a coherent light source. As used herein, the term, "bright" indicates that the light source provides a higher flux of photons than the conventional thermal light source. FIG. 2 compares the flux of photons from a bright synchrotron radiation-based source and the conventional thermal source.

In another embodiment, a controller is used to maintain optimal performance of the source. In yet another embodiment, the source is separated and separately controlled from the tuning system. In another embodiment, the source is coupled to a spectrophotometer, preferably an FTIR spectrophotometer, for calibration purposes.

Suitable mid-IR sources that may be used include but are not limited to free-electron lasers (FEL), DFG (Difference Frequency Generation) sources, tunable mid-IR diode lasers (e.g., Pb-salt diode lasers, quantum cascade lasers), gas or chemical lasers, rare-earth-ion lasers, solid state lasers by transitional metal doped II-VI compounds, or the SDL TC40 IR fibre laser, or thermal emission elements, or other sources that can deliver continuous/broadband infrared light over suitable mid-range IR wavelengths. In some embodiments, wherein the source is tunable, the source 110 can include a tuning system. In one embodiment, where the mid-IR wavelength region chosen is longer than 3 microns, suitable types of tunable diode lasers that may be used, include quantum cascade lasers (QCLs) which operate at or near room temperature, and lead-salt lasers (Pb-salt) which require operation at cryogenic temperature.

An alternative light source is a synchrotron source. Such an IR light source was used in the experiments described below. The synchrotron beam line 1.4.3 at the Lawrence Berkeley National Laboratory (LBNL) Advanced Light Source (ALS) was used because it delivers coherent IR radiation with a brightness in the range of approximately $10^{11}$ to $7 \times 10^{12}$ photons/sec-mm2 mrad-0.1% BW over different wavelengths, which is 100-1000 times brighter than the conventional thermal source employed in regular MIR spectroscopy.

In a preferred embodiment, any source 110 used in the present apparatus should be capable of directing light through a source fiber or optical probe 150 to an area of tissue at a specified location 140, thereby producing a signal with sufficient signal to noise ratio. A sufficient signal-to-noise ratio would be 3 or higher, more preferably 10 and higher, at a small area or spot size. In a preferred embodiment, the area of tissue can be from one to several $\mu m^2$ to several hundred $\mu m^2$ in size, or an area smaller or larger than the typical diameter of a mammalian cell. For example, the area of tissue can range from 1 $\mu m^2$ to 100 $\mu m^2$ up to 10 $cm^2$.

To take advantage of minimum scattering and autofluorescence in biological tissues, several measures can be taken. In one embodiment, the source 110 can be coupled together with an appropriate detector 120, a detection fiber 160 and source fiber 150 with minimum dispersion at the selected wavenumbers. The source fiber 150 is used to carry light from the optical source 110 to the vascular interrogation site and the detection fiber 160 carries reflectance light back to the detector 120. In another embodiment, it is contemplated that the catheter has multiple source fibers 150 and multiple detection fibers 160 to interrogate a tissue at multiple wavenumbers in successive or simultaneous timepoints.

In a preferred embodiment, the detection fiber 160 and detector 120 in the light carrying catheter may be a single or array of detection fibers and a single or array of detectors. In one embodiment, the fiber is a fiber optic cable, for example, C1 Chalcogenide for mid-infrared 2-11 microns, C3 Chalcogenide for mid-infrared 2-6 microns, or Silver Halide for mid-infrared 4-18 microns or fiber optic cable coated with reflective molecules or the like.

The detection fiber 160 in the optical probe may comprise about 21 to 46 fibers. Those having skill in the art will recognize that the number of fiber arrays may be more or less, and that the length and total diameter of the probe, and the types of detection fibers may change according to teachings in the art. In another embodiment, the probe and detectors used in the catheter are those as described in Utzinger, et al, in U.S. Pat. No. 6,571,118, which is hereby incorporated by reference in its entirety.

In one embodiment, the detector 120 or probe has a tip 180 comprising a focal-plane array, a mid-IR chemical camera, or an attenuated total reflection (ATR) tip, or combinations thereof. An example of a detector tip array is shown in the detail in FIG. 1B. The probe will provide chemical-imaging information. If the detector tip 180 is an ATR tip, at least one signal beam should be introduced into an IR transparent crystal in such a way that it is incident on the internal surface at an angle which is below the critical angle, leading to total internal reflection. The geometry is set up so that many reflections or "bounces" occur before the beam exits the crystal. At each bounce an evanescent wave penetrates the medium surrounding the crystal and thereby samples the spectrum of the medium (or cell) adjacent the crystal. In a preferred embodiment, the ATR tip used is DuraDisk produced by SENSIR, which was used in the present examples.

In another embodiment, detector performance will be better increased by thermoelectric (TE) cooling or by the use of an immersion lens or both. Additionally, an $LN_2$ cooled photovoltaic or photoconductive mercury cadmium telluride (MCT) (HgCdTe) detector can be used. For example, the infrared detectors for 1.5 to 12 microns can be quantum or thermal infrared detectors whose sensitive wavelength begins in the visible or within around 1 $\mu m$ to 10 or more microns of the longest wavelength, which can be increased by TE cooling. In one embodiment, the system may have DC-coupled preamps for photovoltaic detectors or AC-coupled preamps for photovoltaic or photoconductive detectors to generate customized bandwidth or special gain for the preamp.

In another embodiment, detector performance can be increased by converting the reflectance signal at the distal end of the catheter or at or near the tip 180 using a transducer system as is known in the art. By placing a transducer system at the distal end of the catheter and converting the optical signals to electrical signal can prevent weak signals from being lost. This electrical signal can be further amplified by the transducer system.

Referring again to FIG. 1B, the reflected IR spectrum is generated by a computer means 130. The light that the sample reflects or transmits is collected by the detectors 120, and then processed by a computer means 130. In one embodiment, the computer means 130 is also preferably a controller device which can also control, sense and record data collection of the catheter. In another embodiment, the computer means 130 can also control fiber movements of the catheter 200 and the tip 180 within the subject.

In one embodiment, the reflectance collected by the detectors 120 is processed by the computer means 190 via a Fourier transform to produce an infrared spectrum. The computer means 190 should also be capable of analyzing and comparing the reflectance generated spectrum as described above. In another embodiment, the comparison between the reference spectrum and the reflected IR spectrum is carried out by software on the computer. Having stored reference numbers allows the device to generate a pre-interpreted output In a preferred embodiment, the computer means 190 should contain at least the reference wavenumbers described in Table 1 for comparison and analysis. Commercially available software can also be used by the computer means 190 to analyze the reflectance generated spectrum including but not limited to, CYTOSPEC (Cytospec, Inc., Croton-on-Hudson, N.Y.), OMNIC Spectroscopy Software Suite (Thermo Electron Corporation, Waltham, Mass.), ORIGIN (Northampton, Mass.), and ImageProsoftware.

Each individual component is known separately in the art. Thus it is contemplated that each component may be varied by use of the teachings of the present invention and what is known or available in the art. For example, it is contemplated that components described in the apparatus described as in Rava et al., in U.S. Pat. No. 6,697,665, which is hereby incorporated by reference, may be used in the present invention.

Alternative FTIR Instrumentation

In another embodiment, after the computer generates the reflectance generated IR spectrum, the reflectance IR spectrum is compared with a reference spectrum generated in the interferometer 112.

Mid-infrared reflectance generated absorption spectra are obtained by detecting changes in infrared intensity as a function of frequency over the mid-IR molecular fingerprint region of the electromagnetic spectrum. Most commercial instruments accomplish this by using either dispersive or Fourier transform infrared (FTIR) spectrometers to separate and measure infrared radiation. One can use Fourier transform infrared (FTIR) or diffusive reflectance spectroscopy of biological systems to measure the interaction of infrared light with biomolecules. The fundamental measurement obtained is a spectrum of infrared reflectance (associated with energies that are not absorbed) and may be expressed as absorbance in the sample as a function of the wavelength of IR light (typically expressed in units of wavenumbers, $cm^{-1}$). Atoms inside the sample vibrate with characteristic frequencies governed by their chemical bonding environment and as such the measured frequencies of these vibrations (the sample absorbs infrared light when the frequency of the light exactly matches the frequency of the vibration) are unique for every molecular configuration.

FTIR spectroscopy is therefore sensitive to the presence of chemical functional groups (a structural fragment) in a molecule within biological samples. With appropriate interpretation of measured FTIR spectra one can detect, identify, and quantify many molecular species within a biological sample. This FTIR spectroscopy capability has recently been combined with microscopy, which allows one to conduct chemical analysis and map the distribution of chemical species with fine spatial resolution.

Dispersive spectrometers use a monochromator to "single out" a particular wavelength/energy from a broad energy distribution of photons, whereas FTIR replaces the monochromator with an interferometer and collects all wavelengths simultaneously. This results in a substantially higher signal-to-noise ratio (SNR), and has greatly extended the capabilities of infrared spectroscopy and has been applied to many areas that are very difficult to analyze by dispersive instruments.

IR radiation from a broadband source is first directed into an interferometer, where it is divided and then recombined after the split beams travel different optical paths to generate constructive and destructive interference. Next, the resulting beam passes through the sample compartment to reach to the detector. The intensity of radiation reaching the detector varies in a sinusoidal manner to produce an interferogram output. The interferogram is the record of the interference signal. If the sample happens to absorb at this frequency, the amplitude of the sinusoidal wave is reduced by an amount proportional to the amount of sample in the beam.

The interferogram contains information over the entire mid-IR region to which the detector is responsive. Employing Fourier transformation converts the interferogram (a time domain spectrum displaying intensity versus time within the mirror scan) to the final IR spectrum, which is the frequency domain spectrum showing intensity versus frequency.

The detector signal is sampled at small, precise intervals. The sampling rate is controlled by an internal, independent reference, a modulated monochromatic beam from a laser focused on a separate detector.

Examples of an interferometer that may be used in the apparatus herein described is an IR Spectrophotometer such as the Nicolet Magna 760 with Nic-Plan IR Microscope, or the ThermoNicolet Nexus 870. Interferometers are generally used when observing over a broad spectrum of data, such as when a synchrotron is the source. The mid-infrared sources used in conventional FTIR instruments are thermal emission elements that produce a graybody spectrum from a filament heated to 1000 to 2000 K These elements are physically large (at least several millimeters), and typically radiate in all directions. The optics of the FTIR bench collect and collimate the light, pass it through the scanning interferometer, and then on to the all-reflecting IR microscope where the modulated IR light is focused to a small spot on a sample. Finally, the light that the sample reflects or transmits is collected, focused onto an appropriate infrared detector, and processed by a computer via a Fourier transform to produce an infrared spectrum.

In another embodiment, where the IR source is a synchrotron, the working of synchrotron infrared reflectance (SIR) spectromicroscopy is very similar to any conventional FTIR spectromicroscopy workstation, except for its photon source. The high brightness of synchrotron IR ("SIR") spectromicroscopy facilities capable of generating a signal to noise ratio several orders of magnitude greater than thermal IR sources for small samples (FIG. 2), enables a multitude of new scientific applications. For the study described in the Examples using SIR, a minimum signal to noise ratio of at least 20:1 is required for a spot size of 10 micron (in diameter).

The present method and apparatus is not limited to use with a synchrotron IR source. Other IR sources which deliver the required signal to noise ratio may be used, such as DFG (Difference Frequency Generation), and/or tunable mid-IR diode lasers (e.g., Pb-salt diode lasers, quantum cascade lasers), or gas & chemical lasers, or rare-earth-ion lasers, or solid state lasers by transitional metal doped II-VI compounds, or the SDL TC40IR fibre lasers, or other sources.

In spite of the high brightness of SIR beam, mid-IR photons are too low in energy (0.01-1.0 eV) to either break bonds or to cause ionization. It is important to use light that does not cause ionization when introduced in vivo. The SIR beam has no detectable effect on the short- and long-term viability, reproductive integrity, cell-cycle progression, and mitochondrial metabolism in living human cells, and produces only minimal sample heating (<0.5° C.). The SIR spectromicroscopy technique is therefore ideal for the characterizing and studying of small and/or heterogeneous samples, for example; individual living cells, microorganisms, and larger biological systems in which local biochemistry may have significant spatial variations such as vulnerable plaques in aorta.

Thus there has been described an apparatus for obtaining reflectance generated spectrographic readings from a location within tissues of a living organism. In a preferred embodiment, the apparatus comprises a source of broad-band mid-IR light, a computer having a recording and/or display means, and a catheter optically coupled to the source for delivering and returning mid-IR light and a detector having a detector tip on an end of the catheter for placement adjacent a sample. If the source is a laser system that generates photons with a single wavenumber or with a narrow-band mid-IR light, the apparatus would comprise a source; a controller or the like, to maintain optimal laser performance and control the source; a detector; and a computer. One should employ a spectrophotometer, preferably an FTIR spectrophotometer, for calibration purposes.

The present invention is particularly adapted for use in the diagnosis of atherosclerotic plaques. A method for obtaining spectrographs in the mid-IR region and interpreting these results relative to the condition of a tissue, such as an arterial wall, contacted with the probe has been described. One or more peaks may be selected for detection and reference, and the peaks may be represented and analyzed in a variety of ways known in the art.

Example 1

Intravascular Mid-IR Spectromicroscopy Studies of ApoE Mice

This study characterizes specimens from apolipoprotein E (ApoE) knockout atherosclerotic mice (Francis Blankenberg, Stanford University, CA) by using intravascular mid-IR spectromicroscopy to observe the selected marker segments in the spectrograph and measure the chemical functional groups found in the specimens by reflectance generated absorbance spectroscopy. These functional groups were then related to the unique biological and chemical processes associated with the pathology of vulnerable plaques. For comparison, specimens from normal mice (Swiss) and rats (Sprague-Dawley) were treated with turpentine injection into the thigh muscle to create a model of sterile soft tissue abscesses. Results from the ApoE knockout mouse are presented in FIGS. 3-6, whereas results from the mice and rats are presented in FIGS. 7-10.

A. Experimental Set-up.

All MIR spectromicroscopy measurements of the ApoE-deficient mouse aorta were carried out at the LBNL ALS. The light source used in these experiments described below is the synchrotron beam line 1.4.3 at the Lawrence Berkeley National Laboratory (LBNL) Advanced Light Source (ALS). This beam line delivers coherent IR radiation with a brightness in the range of approximately $10^{11}$ to $7\times10^{12}$ photons/sec-mm2 mrad-0.1% BW over different wavelengths.

The FTIR interferometer used in this experimental system operates as described above. Imaging experiments were also conducted using the thermal emission elements, which can be focused to as fine as 10-μm in diameter with an IR microscope and array detectors.

To measure something smaller, such as localized biological phenomena in biological samples, one must mask away part of the incoming light, significantly reducing the signal strength. This is done by having a true point source focused to a small but not limited to diffraction-limited spot size; with 1/f optics this is approximately the half of the wavelength of the light. This is where using a synchrotron as an IR source provides advantages in the development of the present method.

A synchrotron is a high-energy electron storage ring optimized for the production and collection of the intense light radiated by the electrons upon acceleration. For mid-IR and longer wavelengths, the effective source size for a synchrotron light source is diffraction-limited. In other words, it is very close to an ideal point source. This means that in FTIR spectromicroscopy based on synchrotron radiation, the beam is focused to a small spot and provides several orders of magnitude greater brightness than conventional (thermal emission) IR sources. The sample can be positioned using a computer-controlled x-y-z stage with 0.1 μm precision, allowing mapping measurements of FTIR spectra as a function of x and y position on the sample.

Synchrotron radiation from the bending magnet was collected, collimated, and transported to a commercial FTIR interferometer bench (either the Nicolet Magna 760 with Nic-Plan IR Microscope, or the ThermoNicolet Nexus 870 with Continuum IR Microscope; both systems were $N_2$ purged. After modulation by the interferometer, the commercial infrared microscope focuses the beam onto the sample using all-reflecting optics. Biological samples were placed in an on-stage mini-incubator with environmental controls to precisely monitor temperature and moisture. The sample stage position is computer controlled with 1 micron precision. The reflected light from the sample was collected by the microscope optics and sent to the mercury-cadmium-telluride IR detector which was cooled with liquid $N_2$. A computer performed a Fourier transform on the measured interferogram to obtain an infrared spectrum for each sample location. The computer may also remove characteristic $CO_2$ peaks at 683 to 656 and 2403 to 2272 $cm^{-1}$ and the water vapor fingerprints from the spectra.

B. Apolipoprotein E (ApoE) Mice.

Apolipoprotein E (ApoE) is a ligand for receptors that clear remnants of chylomicrons and very low density lipoproteins. Lack of the ApoE lipoprotein causes accumulation in plasma of cholesterol-rich remnants, which accumulate in the circulation promoting atherogenesis. ApoE-deficient mice (−/−) have been generated for use as a murine model of spontaneous atherosclerosis. These knockout mice also develop gross atherosclerotic disease while on high cholesterol diets. This model is also advantageous as mice develop all phases of lesions found in humans in a time-dependent manner. Foam cell-rich deposition is usually noted by the age of 3 months followed by severe occlusion with repeated intramural plaque hemorrhages, particularly within the brachiocephalic vessels, by the age of 8 months with a 50% incidence of sudden death 28 weeks after initiation of a high fat/cholesterol diet.

Swiss mice and ApoE −/− mice are recognized as an appropriate model for human atherosclerosis. (See, for example, Journal of Lipid Research Fol. 39, 354-368, February 1998, "Radical-induced lipoprotein and plasma lipid oxidation in normal and apolipoprotein E gene knockout (ApoE −/−)mice: ApoE −/− mouse as a model for testing the role of tocopherol mediated peroxidation in atherogenesis." See also, "Introduction of human apolipoprotein E4 "domain interaction" into mouse apolipoprotein E", *PNAS*, Sep. 25, 2001 98(20): 11587-11591). The IR results from mice are readily transferable to human tissue, since the phenotypic expression of atherosclerotic disease in the mouse and human tissues are comparable.

ApoE −/− mice (8-13 months old) were placed on a high fat/cholesterol (1-2%) diet for 3 months. These animals were then sacrificed and their aorta harvested.

C. Mid-IR Reflectance Generated Absorption Spectromicroscopy Identification of Localized Vulnerable Plaques in ApoE-deficient Mice (−/−) Aorta The aorta section to be studied was placed inside the sample holder of the mini-incubator so that the temperature and moisture were held constant during measurement process. Optical microscope images were used as a guide to select areas with potentially interesting information. For example, from the optical microscope images, potential sampling locations with plaque-like materials were identified (FIG. 5).

All infrared spectra from the selected sampling locations of the ApoE-deficient mouse (−/−) aorta were recorded in the standard reflectance mode in the 4,000 to 650 cm$^{-1}$ region, as this region contains unique molecular absorption fingerprints for the chemical functional groups representative of the various pathophysiological stages of atherosclerosis. Every IR measurement consisting of at least 2 co-added spectra at a spectral resolution between 1 to 32 cm$^{-1}$, is compared by ratio to a reference spectrum similarly collected from the most nearby area of the surface that is free of interfering molecules. The comparison was carried out using Equation (II). Any residual water-vapor features remaining in the resultant spectrum was removed by subtracting an appropriate scaled water-vapor spectrum. Liquid water subtraction can be performed whenever necessary. This however, was not necessary in the experiments described herein.

D. SR-FTIR Spectra of the ApoE Mouse Aorta

Reflectance spectra obtained from different locations of the aorta samples of the ApoE-deficient mouse showed extreme spatial heterogeneities. In areas free of plaque-like materials (dark color of FIG. 5B), the MIR spectral signals were "silent" at the level of soft tissue background illustrated in FIG. 3, discussed below.

FIG. 5A is a triple tracer autoradiograph and a visible light photograph of the same atherosclerotic mouse aorta. These images illustrate the correlation between the results of the present method and other radionuclide contrast agent-based imaging techniques. Aortic autoradiographs obtained after co-injection of annexin-Tc99 m (a marker of apoptosis), FDG-F18 (a marker of metabolic activity) and MCP-1-I-125 (a marker of monocytes and macrophages) one hour after tail vein injection showed selective localization with regions of atherosclerotic plaque. One area of the aorta (taken from the apoE knockout mouse), illustrated by a box 31 in FIG. 5A and magnified in FIG. 5B, was studied both microscopically and with the present MIR technique.

Figure 6:
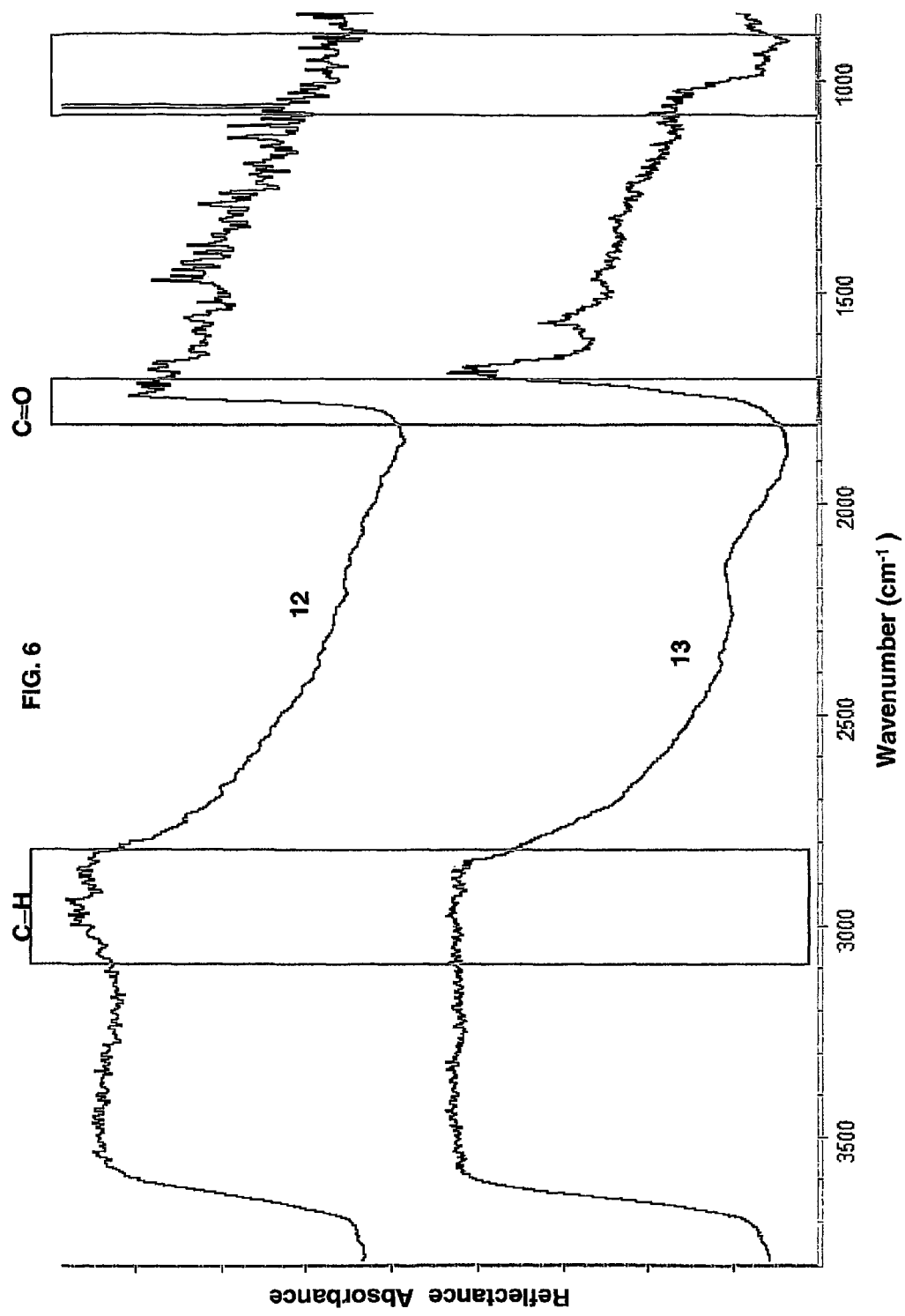
FIG. 6A-6B presents reflectance and reflectance generated absorption spectrographs from sampling points 12 and 13 as depicted in FIG. 5B, which are in an area being free of atherosclerotic plaque.
Figure 7:
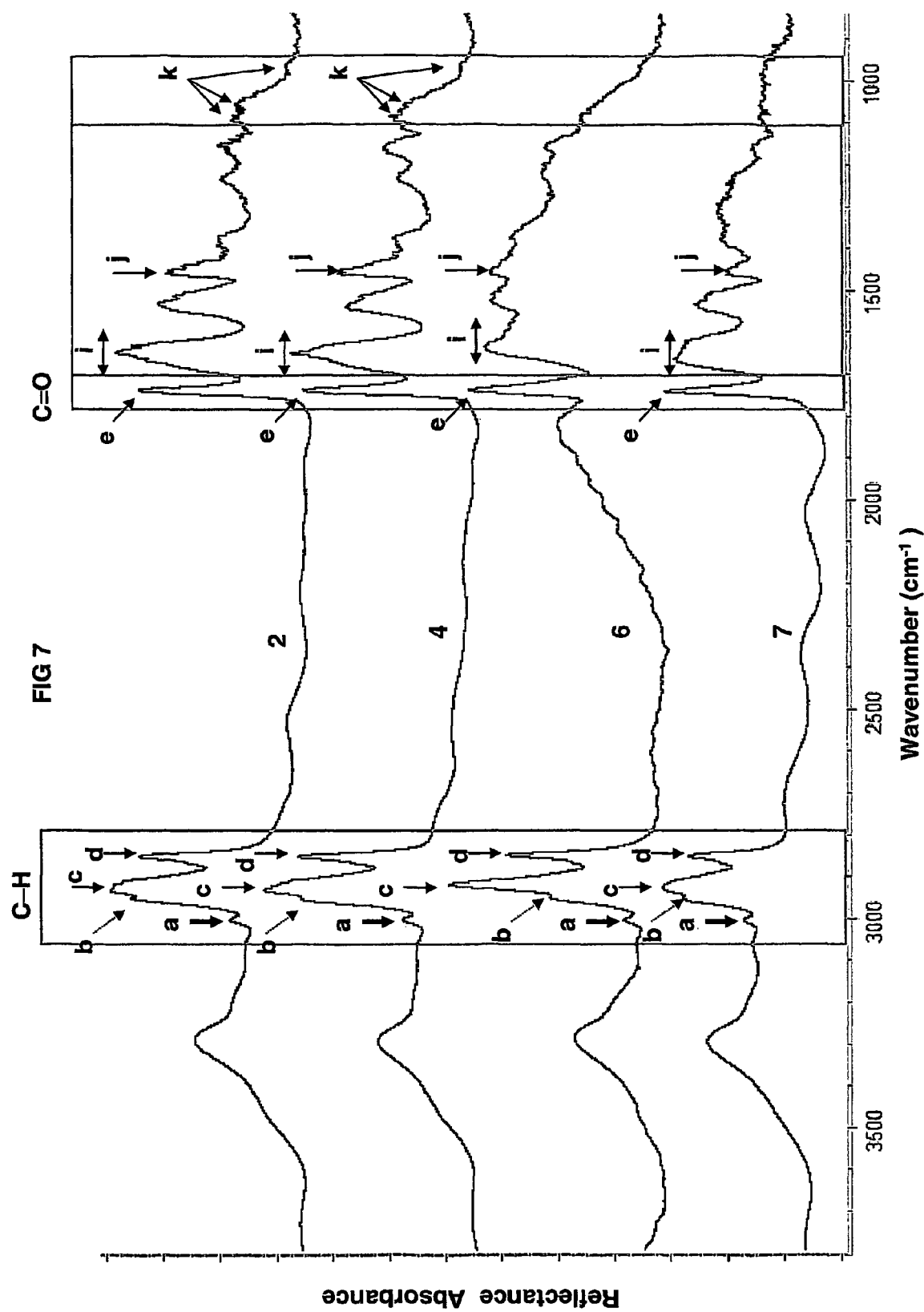
FIG. 7 presents reflectance generated absorption spectrographs for locations 4, 2, 6, and 7 as depicted in FIG. 5B, an area of the aorta with vulnerable atherosclerotic plaque.
Figure 8:
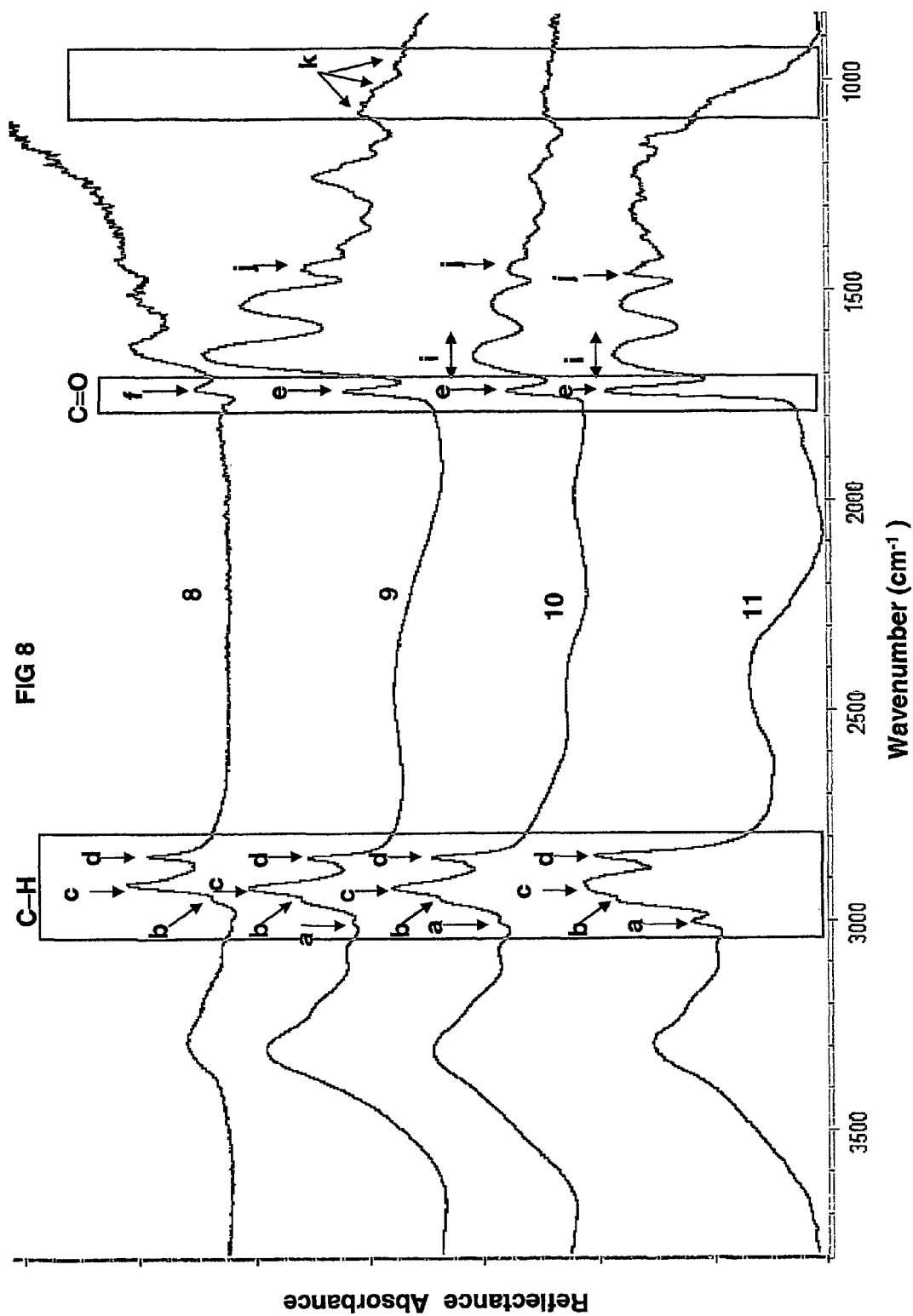
FIG. 8 presents a reflectance generated absorption spectrograph for locations 8, 9, 10 and 11 of FIG. 5B, an area of the aorta also with vulnerable atherosclerotic plaque.

As can be seen in FIG. 5B, the area of box 31 is heterogeneous, containing both atherosclerotic and non atherosclerotic regions. The numbers 1 through 12 indicate different sampling points in this region. Each sample covers a 10 micrometer spot. The scale bar is 50 micrometers. Mid-IR spectral signals from these sampling points indicate that vulnerable plaques are a highly localized phenomenon. FIG. 6 illustrates the Mid-IR spectrograph from points 12 (6A) and 13 (6B); FIG. 7 illustrates the Mid-IR spectrograph from points 2, 4, 6 and 7; and FIG. 8 illustrates the Mid-IR spectrograph from points 8, 9, 10 and 11.

Referring now to FIG. 4, there are shown four different tracings, offset on the y axis for clarity. The top tracing represents aorta tissue without vulnerable plaque. It was obtained a section of the ApoE-deficient mouse (−/−) aorta that lacked vulnerable plaque. The next tracing below represents vulnerable plaque (i.e., plaque subject to rupture, containing lipid droplets, macrophages and apoptotic cells). These tracings are discussed in detail in connection with FIGS. 6 and 7. Below that is a tracing obtained from a scan of lipid droplets, indicating those characteristic peaks, and at the bottom is a tracing obtained from inflamed macrophages in a non-atherosclerotic model (i.e. the turpentine model). Peak "h" in the bottom tracing indicates the presence of an acidic (highly protonated) environment associated with a highly active macrophage "dissolving" the turpentine-injured tissues. The first region illustrated is the C—H bond region, in the vicinity of wavenumbers 3000-800. Peaks a, b, c and d are indicated in FIGS. 7 and 8.

The wavenumbers for the peaks are as follows. Note that the wavenumbers are approximate, and the actual peak value may be at least 15 wavenumbers above or below the denoted peak value.

a: ~3007 cm$^{-1}$
b: ~2950 cm$^{-1}$
c: ~2916 cm$^{-1}$
d: ~2852 cm$^{-1}$
e: ~1743 cm$^{-1}$
f: ~1739 cm$^{-1}$
g: ~1740 cm$^{-1}$
h: ~1725 cm$^{-1}$
i: ~1678 and 1620 cm$^{-1}$
j: ~1467 cm$^{-1}$
k: ~1090, 1052, and 965 cm$^{-1}$ As can be seen in FIG. 4, the spectra in Trace A taken in the C-H region, i.e. wavenumbers 3000-2800, in normal tissue is relatively flat, while in vulnerable plaques, peaks a, b, c, and d in the same region are readily determined in Trace B. Peaks c and d may be seen in lipid droplets (Trace C); peaks b, c, and d may be seen in inflamed macrophages (Trace D). The unique spectral markers within the 3600-2800 cm$^{-1}$ region and the 1750-1500 cm$^{-1}$ region are also visible in the Figure.

Referring now to FIG. 6, a spectrogram of reflectance vs. wavenumber is shown for tracings 12 and 13. By comparing these tracings to FIG. 4, it can be seen that these spots represent normal arterial wall. FIG. 6 is characterized by broad featureless peaks in the vicinities of 2800 to 3400 and 1700 to 1000, similar to the top tracing in FIG. 4. The absorbance in normal tissue has values often exceeding 2 units, which is generally considered as spectroscopically "silent". This is because of the high absorption of infrared photons by the cardiac-muscle cells, which is expected from our experience. The overall spectral pattern and the simultaneous presence of amide I (~1648 cm$^{-1}$) and amide II (~1548 cm$^{-1}$) peaks recorded at location #13 indicate the possible presence of non-cardiac-muscle cells.

In FIG. 7, tracings 2, 4, 6 and 7 are shown. These four tracings are from spots in FIG. 3B that show atherosclerotic plaque. One may observe the characteristic sharp peaks at a, b, c and d as described in FIG. 4. FIG. 7 also shows a series of peaks e, i, j, and k that that are either higher or differently shaped in the region of vulnerable plaques. Note that some blood apparently has interfered with the reading of spot 6, as indicated by peak i characteristic of protein. Peak i in this case is equal in height to the adjacent peak.

In FIG. 8, tracings 8, 9, 10 and 11 are shown. These spots are also from plaques that are vulnerable. The tracings can again be seen to be consistent with the characteristics pointed out above. Again there are distinct peaks in the region 3000 to 2800 and 1800 to 1600. In spot 8 (top line), the trailing upward towards the lower wavenumber 1000 is considered indicative of a necrotic cell (rather than an apoptotic cell).

Example 2

Intravascular Mid-IR Spectromicroscopy Rabbit Studies Performed In Vivo AND Ex Vivo Retired female breeder Watanabe heritable hyperlipidemic (WHHL) rabbits (Covance Research Laboratories, Princeton, N.J.) greater than 12 months in age are placed on a high fat/cholesterol (2%) diet for 0 or 3 months (Certified Rabbit Diet 5322, LabChows®, Purina Mills, Inc.). 5 animals per time point are studied.

An apparatus shown schematically in FIG. 1B can be used to generate intravascular mid-infrared reflectance generated absorption spectra by detecting changes in infrared intensity as a function of frequency over the mid-IR molecular fingerprint region of the electromagnetic spectrum. A mid-IR light source is connected to a detector having a controller, and to a computer which also serves as an output controller and/or processing means. The IR light source also can be optically connected to a Fourier transform infrared (FTIR) or diffusive reflectance spectroscopy interferometer.

A 5 French catheter sheath will be connected to the detectors and the source. The catheter is comprised of a detection fiber and a source fiber, having a detector tip. The catheter is inserted into the lumen of a rabbit artery or other tissues suspected of containing physiological markers indicative of vascular disease or other inflammatory conditions.

Each animal will undergo intra-arterial catheterization with a 5 French catheter sheath through of a femoral artery through which the mid-IR catheter will be placed into the root of the aorta. The mid-IR catheter will then be precisely rotated and withdrawn in spiral mode to acquire a mid-IR spectral map of the thoracic and abdominal aorta. The source emits a signal that is transmitted through the source fiber and emitted at the intravascular interrogation site. The detector tip detects the reflectance generated light after it has been reflected and absorbed by the surrounding tissues and transmits the signal through the detection fiber to the computer.

The animal will then be sacrificed and the thoracic and abdominal aorta with their side braches will be carefully dissected, removed, incised longitudinally along the anterior long axis of the aorta and layed out flat mounting media for ex vivo mid-IR and histologic analyses at LBNL. The in vivo mid-IR spectral map can be reformatted and flattened out into a 2 dimensional format oriented in the same fashion as the incised aorta. The 2 dimensional mid-IR spectra from the in vivo and ex vivo IMIR studies will then be directly and systematically compared digitally in order to determine the in vivo sensitivity and resolution of the mid-IR catheter and its correlation with the histologic and biochemical features of atherosclerotic plaques.

The ability of the mid-IR catheter of FIG. 1B and FIG. 1C to detect decreases in the severity of atherosclerotic plaques in response to statin cholesterol lowering therapy can be assessed in vivo. In two separate groups of animals after the period of high fat/cholesterol diet and the drawing of serum triglyceride and cholesterol levels animals are placed on a normal diet and receive one month of statin therapy with atorvastatin, 20 mg/kg/day in drinking water according to a modification of the model of Weis et al., "Statins have biphasic effects on Angiogenesis," *Circulation* 2002; 105:739-745. Animals will then have repeat triglyceride and cholesterol levels drawn and are imaged with the mid-IR catheter in vivo and ex vivo in the same manner as untreated rabbits as described above.

Example 3

Ex Situ Animal and Human Tissue Studies Using IMIR

Rabbit and human tissues from normal and atherosclerotic aortas supplied by a cardiologist are analyzed as described in the previous Examples. In addition, the apparatus described in Example 2 and shown in FIG. 1B is used with a Continuμm XL FT-IR imaging microscope (Nicolet Thermo-electron corporation) which is equipped with both infrared and ATR objectives. The apparatus is used to image mid-infrared spectra of aorta specimens from rabbits and humans. Infrared spectral signatures from different types of plaques, such as thick plaques, plaques with grossly intact endothelial surface, etc., will be interrogated using the methods as described in Examples 1 and 2. The rabbit tissues are similar to the tissues described in Example 2. The human tissues are harvested arterial tissues from human patients having vascular disease and suffered from sudden cardiac death. The pathologies of these tissues are known. Therefore, the spectra obtained from these tissues can be readily confirmed by a pathologist. Using the mid-IR peaks disclosed in Table 1, a diagnosis of whether the tissues contain vulnerable plaques and at which specific locations are obtained by observing the spectra at each location interrogated. The diagnosis should match that of the pathologist, whose conclusion was obtained by using light microscopy. Each tissue is classified as normal or containing vulnerable plaques using standard diagnostic criterion.

The spectral signals obtained from tissues having plaques will be compared with normal tissues that do not have plaques. The results then will be validated by histological analysis.

Example 4

Clinical Trials Using IMIR

Reflectance spectra will measured by intravascular mid-IR spectroscopy in volunteers with no history of coronary or aortic atherosclerotic disease at specified distinct clinically normal sites in intravascular tissues using the apparatus similar to that described in Example 2 and 3. The spectra taken of intravascular tissues from the normal patients will be compared to spectra taken of patient with a known or suspected coronary and aortic atherosclerotic disease.

Following initial screening in a patient with a known or suspected coronary and aortic atherosclerotic disease, reflectance spectra is measured in least 2-5 interrogation sites. Each patient will undergo intra-arterial catheterization with a catheter sheath through a femoral artery through which a mid-IR catheter will be placed into the root of the aorta The catheter may have a camera on its distal end used for visual inspection of the tissues. The mid-IR catheter will then be precisely rotated, inserted and withdrawn, preferably in spiral mode, to acquire a mid-IR spectral map of the thoracic and abdominal aorta. The reflectance of each interrogation site is measured. In addition to the two to five abnormal sites, reflectance spectra are measured from one to three neighboring normal sites. Post-spectroscopy, abnormal sites are again probed using a catheter and known techniques such as intravascular ultrasound, to obtain angiographic images to assess lesion and plaque morphology and severity. A clinical diagnosis of each lesion or plaque as normal or vulnerable and recorded by an experienced vascular pathologist. During follow up surgeries, a 2-4 mm biopsy of the tissue may be taken from the interrogated area. These specimens are evaluated by an experienced pathologist using light microscopy and classified as normal or containing vulnerable plaques using standard diagnostic criterion. Biopsies with multiple diagnoses will be classified according to the most severe pathological diagnosis. The pathologist and clinicians may be blinded to the results of the spectroscopic analyses.

The spectra from the normal patients and the suspected diseased patients will be compared. Using the mid-IR peaks disclosed in Table 1, the physician should be able to diagnose whether the suspected diseased patients have vulnerable plaques in their arteries and at which specific locations. The diagnosis should match that of the pathologists.

The present embodiments described herein in the examples, methods, procedures, apparatus and devices are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference.

REFERENCES FOR TABLE

Barth, A. (2000). "The infrared absorption of amino acid side chains [Review]." *Progress in Biophysics & Molecular Biology* 74(3-5): 141-173.

Chiriboga, L., P. Xie, et al. (1998). "Infrared Spectroscopy of Human Tissue-Li-a Comparative Study of Spectra of Biopsies of Cervical Squamous Epithelium and of Exfoliated Cervical Cells." *Biospectroscopy* 4(1): 55-59.

Gaigneaux, A., J. M. Ruysschaert, et al. (2002). "Infrared spectroscopy as a tool for discrimination between sensitive and multiresistant K562 cells." *European Journal of Biochemistry* 269 (7): 1968-1973.

Hadden, J. M., M. Bloemendal, et al. (1994). "Structure and Thermal Stability of the Extracellular Fragment of Human Transferrin Receptor at Extracellular and Endosomal Ph." *FEBS Letters* 350(2-3): 235-239.

Knells, G., M. K. Ahmed, et al. (1995). "Fourier-Transform Infrared Spectroscopic Analysis of Rabbit Lung Surfactant—Subfraction-Associated Phospholipid and Protein Profiles." *Chemistry & Physics of Lipids* 77(2): 193-201.

Lecoutre, J., L. R. Narasimhan, et al. (1997). "The Lipid Bilayer Determines Helical Tilt Angle and Function in Lactose Permease of *Escherichia Coli*." *Proceedings of the National Academy of Sciences of the United States of America* 94(19): 10167-10171.

Lewis, E. N. and R. N. McElhaney (1996). Fourier transform infrared spectroscopy in the study of hydrated lipids and lipid bilayer membranes. *Infrared spectroscopy of biomolecules*. New York, Wiley-Liss: 159-202.

Lewis, R., M. Kiricsi, et al. (2003). "Fourier transform infrared spectroscopic study of the interactions of a strongly antimicrobial but weakly hemolytic analogue of gramicidin S with lipid micelles and lipid bilayer membranes." *Biochemistry* 42(2): 440-449.

Lewis, R. and R. N. McElhaney (2000). "Calorimetric and spectroscopic studies of the thermotropic phase behavior of lipid bilayer model membranes composed of a homologous series of linear saturated phosphatidylserines." *Biophysical Journal* 79(4): 2043-2055.

Lewis, R., S. Tristram-Nagle, et al. (2001). "The thermotropic phase behavior of cationic lipids: calorimetric, infrared spectroscopic and X-ray diffraction studies of lipid bilayer membranes composed of 1,2-di-O-myristoyl-3-N,N,N-trimethylaminopropane (DM-TAP)." *Biochimica et Biophysica Acta—Biomembranes* 1510(1-2): 70-82.

Liu, K. Z., M. Jackson, et al. (1996). "Modification of the Extracellular Matrix Following Myocardial Infarction Monitored by Ftir Spectroscopy." *Biochimica et Biophysica Acta—Molecular Basis of Disease* 1315(2): 73-77.

Liu, K. Z. and H. H. Mantsch (2001). "Apoptosis-induced structural changes in leukemia cells identified by IR spectroscopy." *Journal of Molecular Structure* 565 (Special Issue SI): 299-304.

Liu, K Z., H. H. Mantsch, et al. (1996). "Infrared Spectroscopic Determination of Hepatic Nuclei Oxidation." *Biospectroscopy* 2(1): 3945.

Liu, K. Z., R. A. Shaw, et al. (2002). "Reagent-free, simultaneous determination of serum cholesterol in HDL and LDL by infrared spectroscopy." *Clinical Chemistry* 48(3): 499-506.

Maleev, V., A. Semenov, et al. (2003). "Spectroscopic and calorimetric study of DNA interaction with a new series of actinocin derivatives." *Journal of Molecular Structure* 645 (2-3): 145-158.

McCrae, K. C., T. Rand, et al. (2001). "Analysis of pulmonary surfactant by Fourier-transform infrared spectroscopy following exposure to Stachybotrys chararum (atra) spores." *Chemistry& Physics of Lipids* 110(1): 1-10.

Mythili, J., T. P. Sastry, et al. (2000). "Preparation and characterization of a new bioinorganic composite: collagen and hydroxyapatite." *Biotechnology & Applied Biochemistry* 32(Part 3): 155-159.

Naumann, D., C. P. Schultz, et al. (1996). What can infrared spectroscopy tell us about the structure and composition of intact bacterial cells? *Infrared spectroscopy of biomolecules*. D. Chapman. New York, Wiley-Liss: 279-310.

Vyavahare, N., M. Ogle, et al. (1999). "Elastin calcification and its prevention with aluminum chloride pretreatment" *American Journal of Pathology* 155(3): 973-982.

Wennerberg, J., E. Kjellen, et al. (1993). "Biochemical Modulation of Chemotherapy and Radiotherapy in Head and Neck Cancer." *Anticancer Research* 13(6B): 2501-2506.

Hoi-Ying N. Holman, Kathleen A. Bjornstad, Morgan P. McNamara, Michael C. Martin, Wayne R. McKinney, and Eleanor A. Blakely, "Synchrotron Infrared Spectromicroscopy as a Novel Bioanalytical Microprobe for Individual Living Cells: Cytotoxicity Considerations," *J. Biomedical Optics*, 7(3), 417424 (2002). And selected for the *Virtual Journal of Biological Physics Research*, 4(3) (2002).

Hoi-Ying N. Holman, Michael C. Martin, and Wayne R. McKinney, "Tracking chemical changes in a live cell: Biomedical Applications of SR-FTIR Spectromicroscopy," *Proceedings of the First International Conference on Biomedical Spectroscopy*, Cardiff, Wales, Jul. 7-10, 2002. *Spectroscopy—An International Journal* 17(2-3), 139-159 (2003).

Hoi-Ying N. Holman, Michael C. Martin, and Wayne R. McKinney, "Synchrotron-Based FTIR Spectromicroscopy: Cytotoxicity Considerations," *J. Biological Physics* 29, 275-286 (2003).

What is claimed is:

1. A method of characterizing subsurface conditions in a tissue, comprising (a) providing a catheter that has a light source that emits light in selected wavenumbers within the range of mid-infrared (IR) spectrum; (b) emitting light in said selected wavenumbers within the range of mid-IR spectrum and directing the light in said selected wavenumbers within the range of mid-IR spectrum from the catheter to an area of tissue at a subsurface location at or below the tunica intima of a blood vessel of a subject; (c) collecting light reflected from the subsurface location and generating a reflectance spectra; and (d) comparing said reflectance spectra to a reference spectra of normal tissue, whereby a subsurface location having an increased number of absorbance peaks at said selected wavenumbers indicates a subsurface tissue inside said blood vessel containing a physiological marker for atherosclerosis, wherein the comparing step comprises that increased numbers of absorbance peaks at said selected wavenumbers are within at least one range of mid-infrared wavenumbers selected from the group of: about 3800-3000 $cm^{-1}$, about 3500-3000 $cm^{-1}$, and about 3020-3000 $cm^{-1}$.

2. The method of claim 1 wherein the comparing step comprises that increased numbers of absorbance peaks at said selected wavenumbers are in the range between about 3000-3100 $cm^{-1}$.

3. The method of claim 1, further comprising the step of generating a spatially resolved map of reflectance generated spectral signals from different locations within a single vessel.

4. A method of characterizing conditions in a subsurface tissue, comprising (a) providing a catheter that has a light source that emits light in selected wavenumbers within the range of mid-infrared (IR) spectrum; (b) emitting light in in said selected wavenumbers within the range of mid-IR spectrum and directing the light in said selected wavenumbers within the range of mid-IR spectrum from the catheter to an area of tissue at a subsurface tissue location in or below the tunica intima of a blood vessel of a subject; (c) collecting light reflected from the subsurface tissue location and generating a reflectance spectra; and (d) comparing said reflectance spectra to a reference spectra of normal tissue, whereby a location having an increased number of absorbance peaks at said selected wavenumbers indicates a subsurface tissue in or below the tunica intima of said blood vessel containing a physiological marker for atherosclerosis, wherein the comparing step comprises that increased numbers of absorbance peaks at said selected wavenumbers is in the range of wavenumbers 4000 to 400 $cm^{-1}$, wherein at least one peak is at about 3300 $cm^{-1}$, or about 3005 $cm^{-1}$.

5. An apparatus for characterizing subsurface tissue conditions, comprising: (a) a single or multiple source of mid-IR light covering a range of mid-infrared wavenumbers; (b) a catheter coupled to said source and a detector to detect light reflected by subsurface tissue in or below the tunica intima of a blood vessel of a subject; (c) a computer means for generating the reflectance generated spectra at selected wavenumbers detected by said detectors and containing the generated spectra to a reference reflectance spectra of normal tissue, to determine whether the subject has atherosclerosis, wherein the selected wavenumbers are about 3800-3000 $cm^{-1}$, about 3500-3000 $cm^{-1}$, and about 3020-3000 $cm^{-1}$ and wherein said computer means has stored therein the reference wavenumber range of 4000-400 $cm^{-1}$.

6. The apparatus of claim 5, wherein said computer means has stored therein at least one of the following reference wavenumber ranges, expressed in $cm^{-1}$: about 4000-2800, about 3500-3000, about 3020-3000, about 2950-2800, about 1760-1710, about 1690-1610, about 1520-1500, about 1480-1450, and about 1100-900 and about 900-400.

7. The apparatus of claim 6, wherein said computer means has stored therein at least one of the following reference wavenumber ranges, expressed in $cm^{-1}$: about 3500-3000, about 3020-3000, and about 1520-1500.

8. The apparatus of claim 5, further comprising an interferometer.

9. The apparatus of claim 5, wherein said catheter comprises a source fiber and a detection fiber having a tip or a tip array, wherein the tip is configured for detecting reflectance generated spectra.

10. The apparatus of claim 5, further comprising a tuning system for said source.

11. The apparatus of claim 5, further comprising a cooling means for said detector.

12. The apparatus of claim 11, further comprising the additional use of customized bandwidth and special gain for DC- and/or AC-coupled preamps for the detectors to increase the signal-to-noise ratio of the detectors.

13. A method of characterizing atherosclerosis in the subsurface of a biological material that has enhanced reflectance and/or spectral features, comprising the steps of: (a) providing light in selected mid-IR wavenumbers between about 4000 to about 400 $cm^{-1}$; (b) directing the light through a probe to a subsurface area in or below the tunica intima of said biological material; (c) measuring reflected light returning through the probe over a range of selected wavenumbers to generate a pattern of spectral signals representative of said area; and (d) comparing spectral signals from a reference spectra to the spectral signals from said area for enhanced reflectance and/or spectral features, wherein said range of selected wavenumbers is selected from the group of: about 3800-3000 $cm^{-1}$, about 3500-3000 $cm^{-1}$, about 3020-3000 $cm^{-1}$ wherein enhanced reflectance and/or spectral features at the selected wavenumbers characterizes said area of said biological material as atherosclerotic.

14. A method of spectroscopic diagnosis of tissue comprising: irradiating a subsurface portion of tissue at a target area at or below the tunica intima in the blood vessel of a subject with radiation having a frequency within the mid-infrared range, transmitted through a fiber optic cable; detecting light reflected by the subsurface area of tissue in or below the tunica intima response to the radiation, the light having a range of 4000 $cm^{-1}$ to 400 $cm^{-1}$; and analyzing the detected reflectance light to diagnose whether the tissue is atherosclerotic including the step of comparing the detected light with reference data, wherein said detected reflectance light is analyzed in at least one of the following wavenumber ranges: about 3800-3000 $cm^{-1}$, about 3500-3000 $cm^{-1}$, and about 3020-3000 $cm^{-1}$.

15. The method of claim 14, wherein the detecting step further comprises collecting the reflected light through the fiber optic cable.

16. The method of claim 14, wherein the irradiation step further comprises a catheter means for insertion of the fiber optic cable in body lumens.

17. The method of claim 14, wherein the fiber optic cable receives light reflected by the tissue and transmits the reflected light to a spectroscopic analysis system.

18. The method of claim 14, further comprising an alternate spectrophotometer to receive the reflected light.

19. The method of claim 14, further comprising the step of rotating the fiber optic cable radially within the blood vessel, whereby data is acquired at various target locations radially within the lumen.

20. The method of claim 19, wherein the steps are repeated thereby performing a 360-degree spectral analysis of the body lumens.

21. A method of detecting vulnerable plaques in a blood vessel tissue of a subject comprising the steps of: delivering mid-infrared light to a subsurface tissue to be diagnosed, irradiating said blood vessel tissue with said light, detecting any delivered light reflected by any vulnerable plaque within the same range as the mid-infrared delivered light, and determining the chemical composition and cellular conditions in the subsurface tissue that indicate vulnerable plaque in a blood vessel in or below the tunica intima, wherein the reflected light is detected in at least one of the following wavenumber ranges: about 3800-3000 cm$^{-1}$, about 3500-3000 cm$^{-1}$ and about 3020-3000 cm$^{-1}$.

* * * * *